(12) United States Patent
Reichman et al.

(10) Patent No.: US 9,994,815 B2
(45) Date of Patent: Jun. 12, 2018

(54) METHODS FOR OBTAINING RETINAL PROGENITORS, RETINAL PIGMENTED EPITHELIAL CELLS AND NEURAL RETINAL CELLS

(71) Applicants: UNIVERSITE PIERRE ET MARIE CURIE (PARIS 6), Paris (FR); CENTRE NATIONAL DE LA RECHERCHE SCIENTIFIQUE (C.N.R.S.), Paris (FR)

(72) Inventors: Sacha Reichman, Paris (FR); Olivier Goureau, Paris (FR); José-Alain Sahel, Paris (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days. days.

(21) Appl. No.: 14/786,427

(22) PCT Filed: Apr. 25, 2014

(86) PCT No.: PCT/IB2014/061010
§ 371 (c)(1),
(2) Date: Oct. 22, 2015

(87) PCT Pub. No.: WO2014/174492
PCT Pub. Date: Oct. 30, 2014

(65) Prior Publication Data
US 2016/0060596 A1 Mar. 3, 2016

(30) Foreign Application Priority Data
Apr. 26, 2013 (EP) ..................................... 13165654

(51) Int. Cl.
| C12N 5/00 | (2006.01) |
| C12N 5/071 | (2010.01) |
| C12N 5/079 | (2010.01) |
| C12N 5/0793 | (2010.01) |
| C12N 5/0797 | (2010.01) |

(52) U.S. Cl.
CPC ........... *C12N 5/0621* (2013.01); *C12N 5/062* (2013.01); *C12N 5/0623* (2013.01); *C12N 2501/115* (2013.01); *C12N 2501/42* (2013.01); *C12N 2502/1323* (2013.01); *C12N 2506/03* (2013.01); *C12N 2527/00* (2013.01); *C12N 2533/54* (2013.01)

(58) Field of Classification Search
None
See application file for complete search history.

(56) References Cited

U.S. PATENT DOCUMENTS

2011/0269173 A1\* 11/2011 Zhu ...................... C12N 5/0621
435/29

FOREIGN PATENT DOCUMENTS

| EP | 2383333 A1 | 11/2011 |
| WO | WO 2012/085348 A1 | 6/2012 |

OTHER PUBLICATIONS

Zhu et al., "Three-Dimensional Neuroepithelial Culture from Human Embryonic Stem Cells and Its Use for Quantitative Conversion to Retinal Pigment Epithelium," PLOS One (2013), vol. 8, Issue 1, pp. 1-13.
Meyer et al., "Modeling early retinal development with human embryonic and induced pluripotent stem cells," PNAS Early Edition (2009), pp. 1-6.
International Search Report for International Application No. PCT/IB2014/061010 dated Aug. 6, 2014.
Tokushige Nakano et al.: Self-Formation of Optic Cups and Storable Stratified Neural Retina from Human ESCs; Cell Stem Cell, Cell Press, US, vol. 10, No. 6, May 4, 2012, pp. 771-785, XP028492663.
Gong J et al.: "Effects of extracellular matrix and neighboring cells on induction of human embryonic stem cells into retinal or retinal pigment epithelial progenitors"; Experimental Eye Research, Academic Press Ltd., London, vol. 86, No. 6, Jun. 1, 2008, pp. 957-965, XP22709066.
Aoki H et al.: "Embryonic stem cells that differentiate into RPE cell precursors in vitro develop into RPE cell monolayers in vivo"; Experimental Eye Research, Academic Press Ltd., London, vol. 82, No. 2, Feb. 1, 2006, pp. 265-274, XP024945331.
Myung Soo Cho et al.: "Generation of retinal pigment epithelial cells from human embryonic stem cell-derived spherical neural masses"; Stem Cell Research, Elsevier, NL, vol. 9, No. 2, May 8, 2012, pp. 101-109, XP028408399.

\* cited by examiner

*Primary Examiner* — Michael D Burkhart
(74) *Attorney, Agent, or Firm* — Merchant & Gould P.C.

(57) ABSTRACT

A method for in vitro obtaining human retinal progenitors, includes the steps of (i) placing an adherent culture of human pluripotent stem cells in a pro-neural medium; and (ii) maintaining this culture in the pro-neural medium until the appearance of pigmented cells and/or of neuroepithelial-like structures. Additional steps can be performed to obtain RPE cells and/or precursors of the neural retina.

18 Claims, 17 Drawing Sheets

Figure 2P:
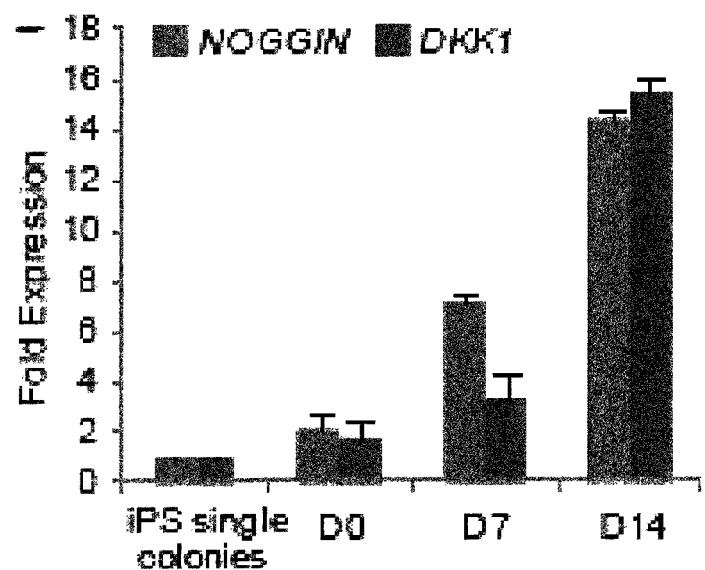

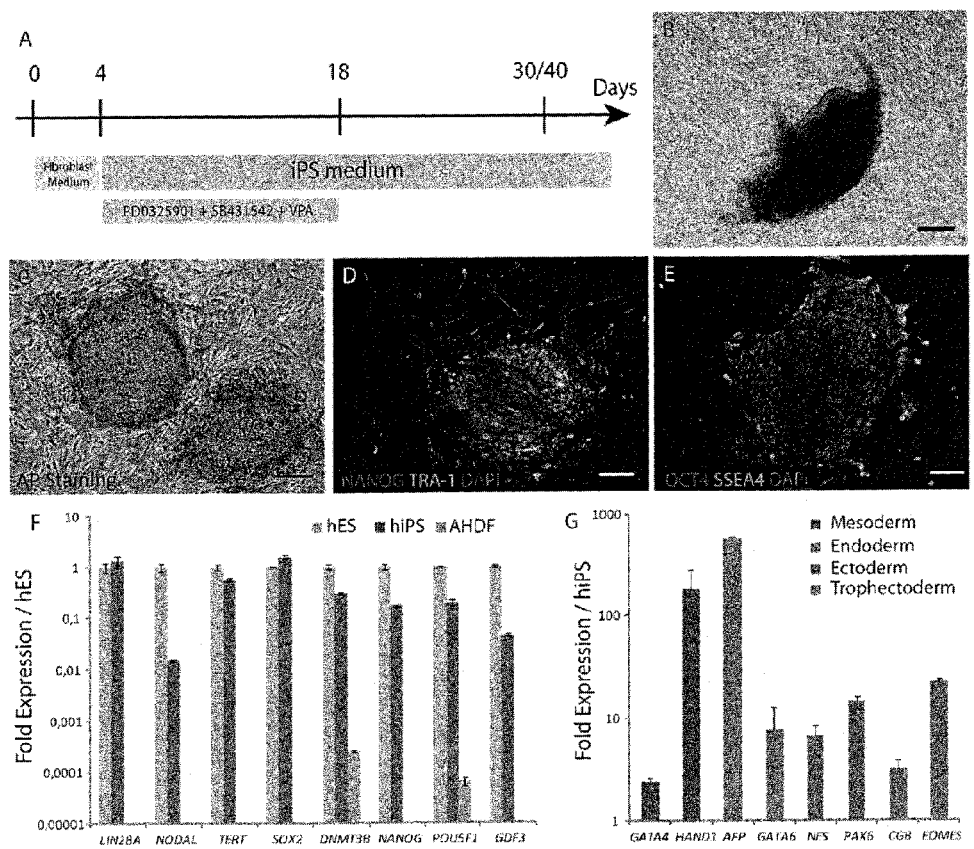
Figure 1A-G

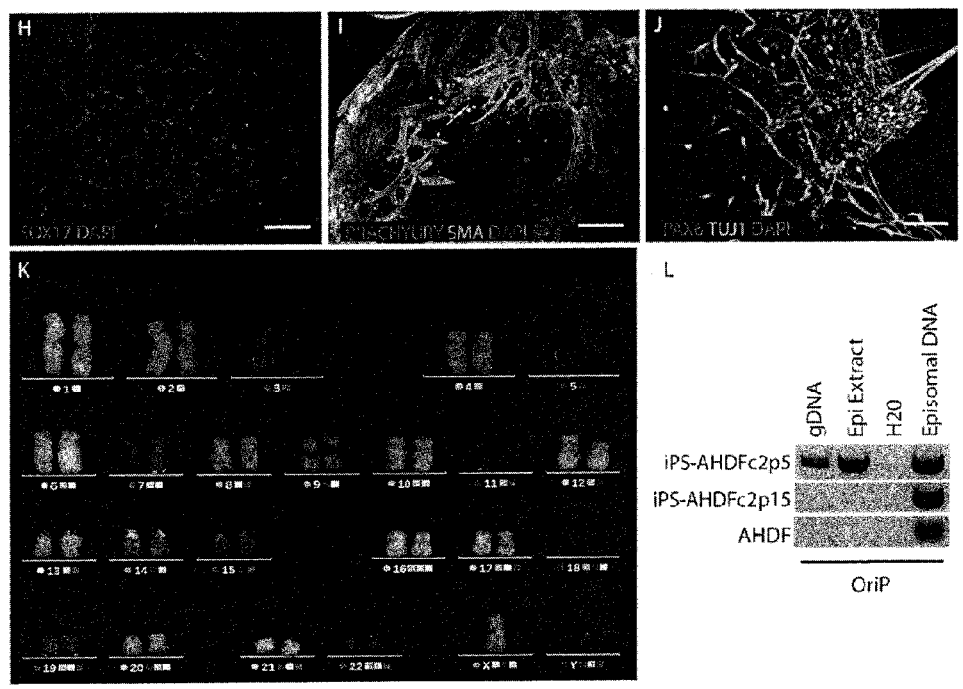
Figure 1H-L

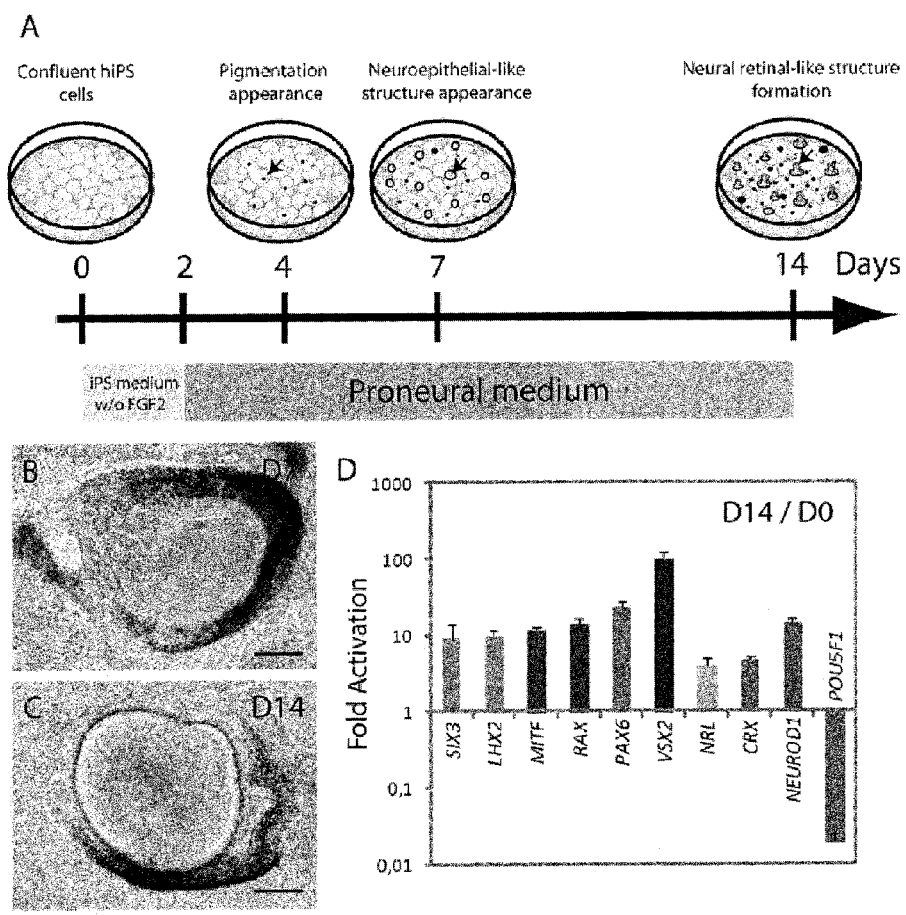
Figure 2A-D

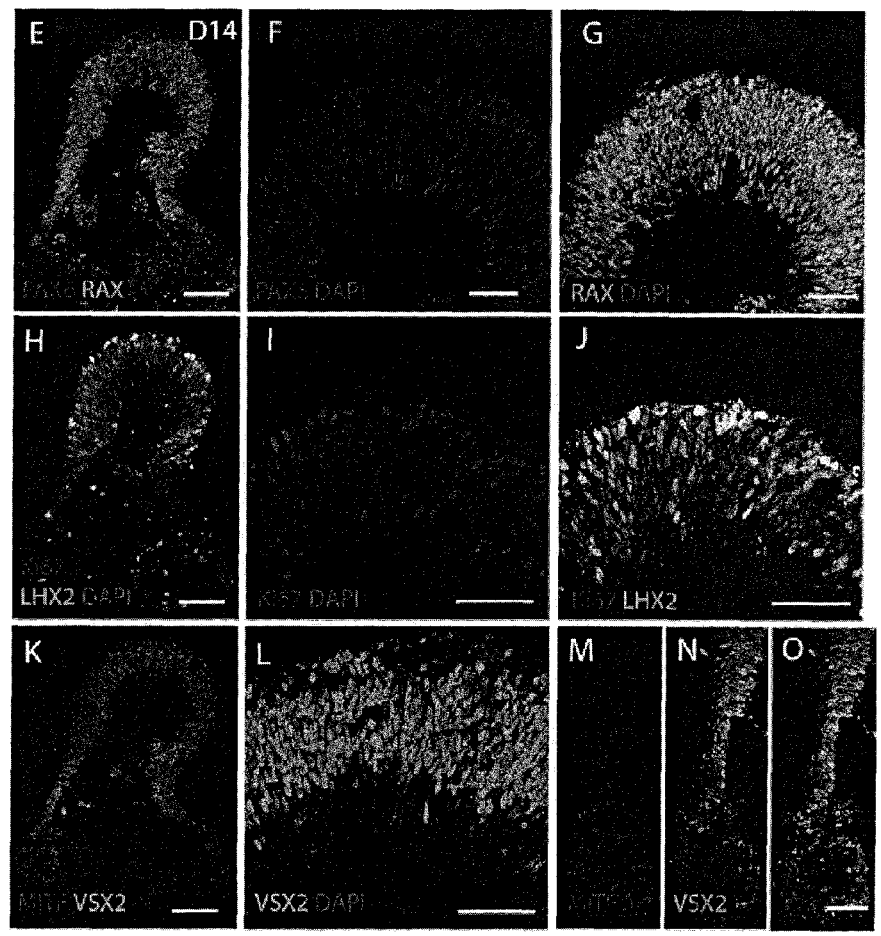
Figure 2E-O

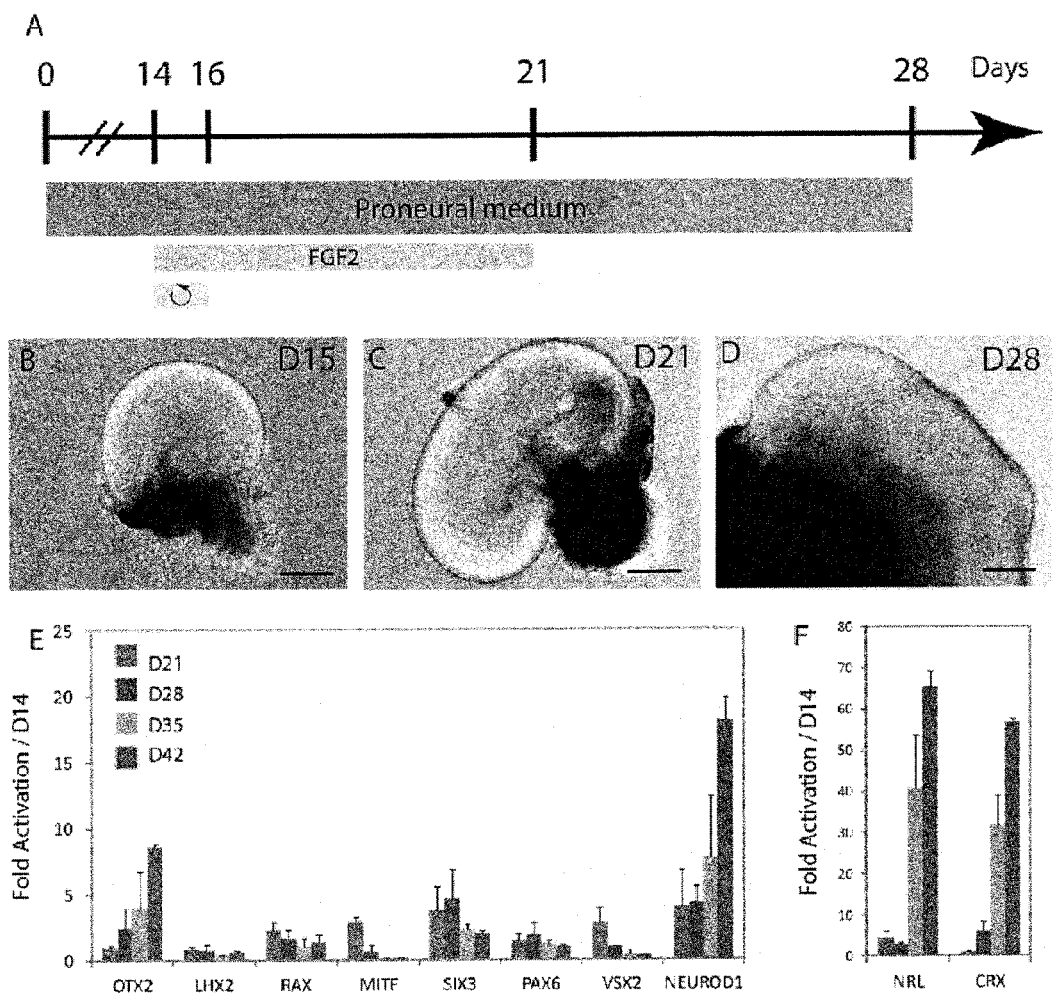
Figure 3A-F

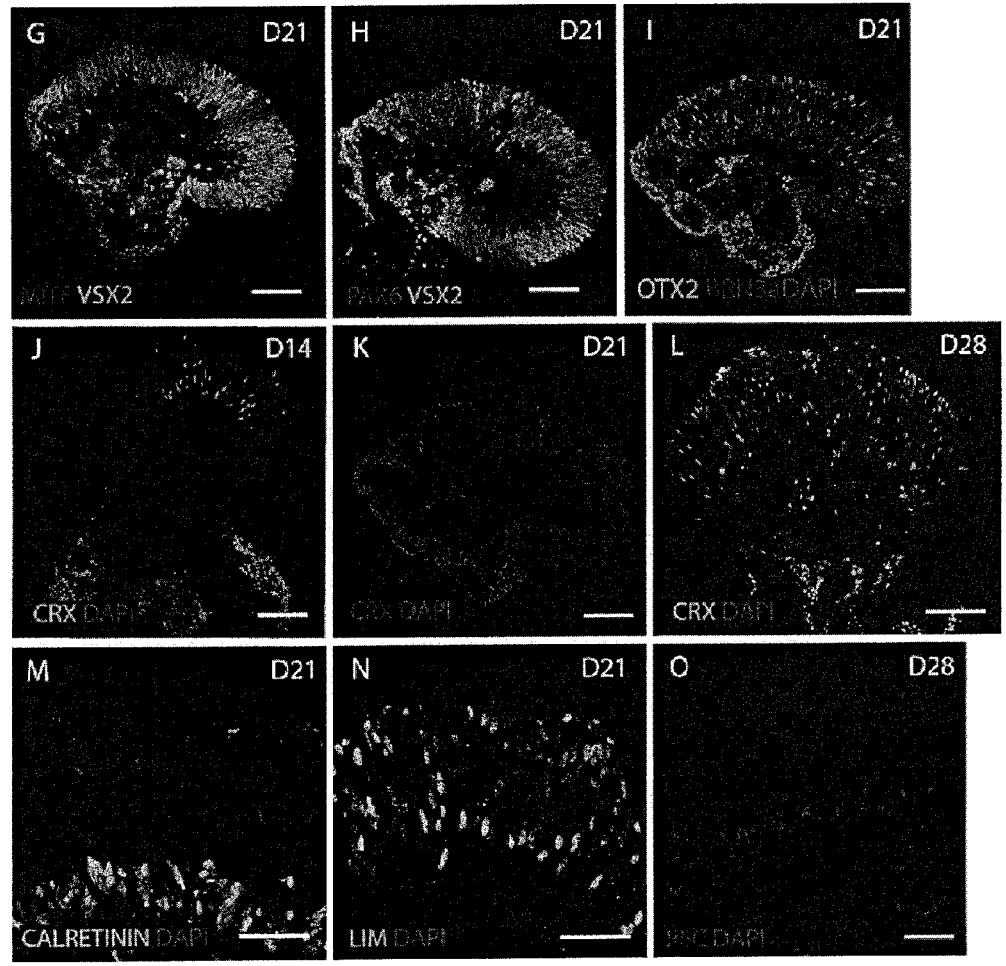
Figure 3G-O

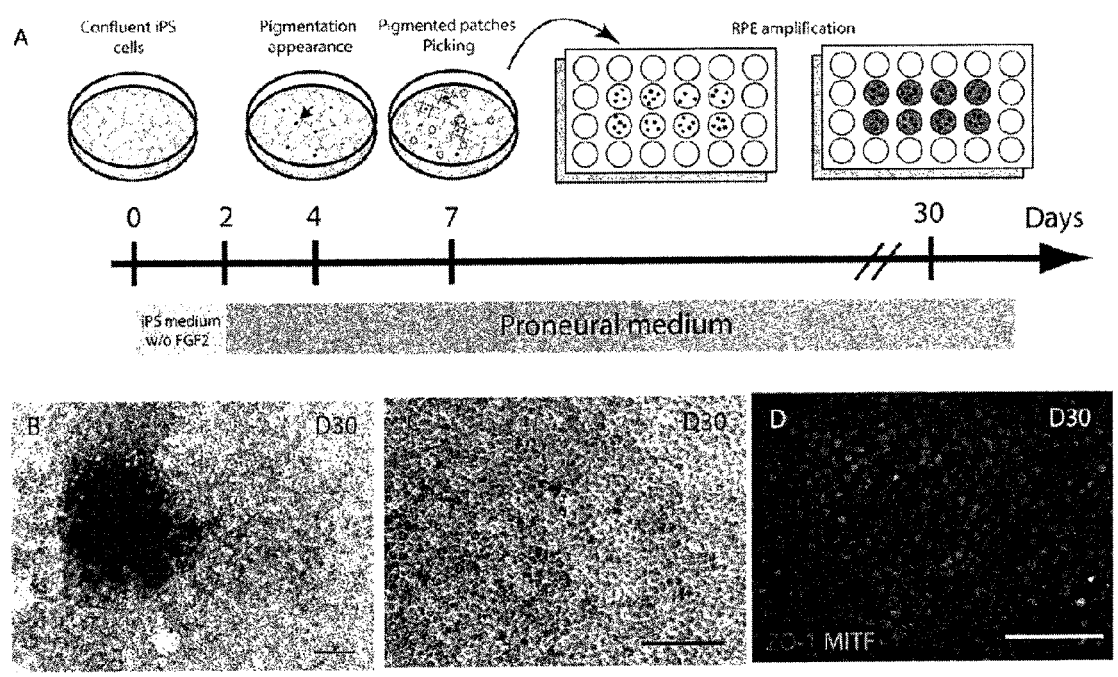
Figure 4 A-D

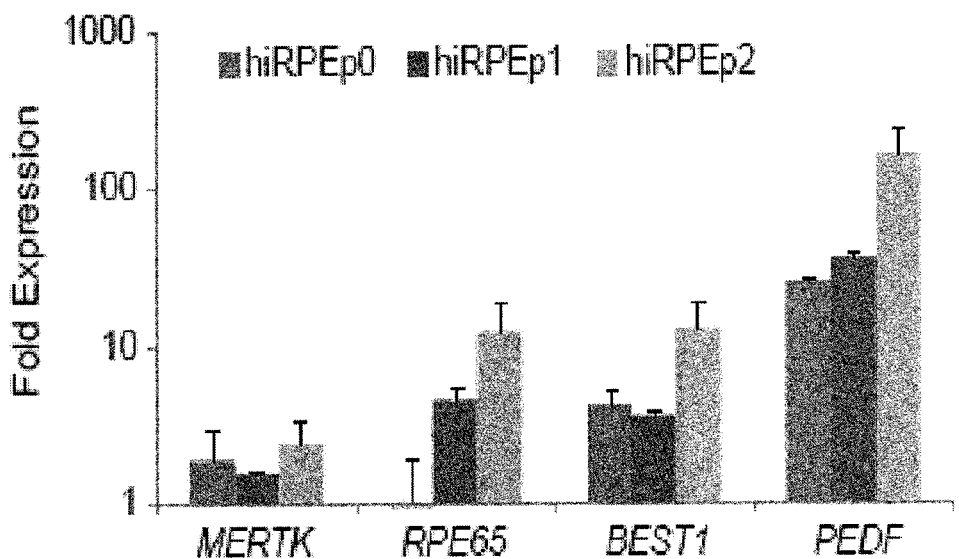
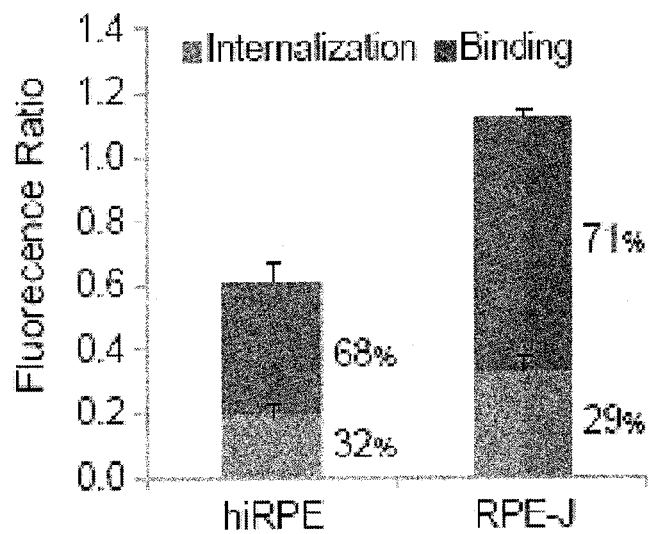
Figure 4E-F

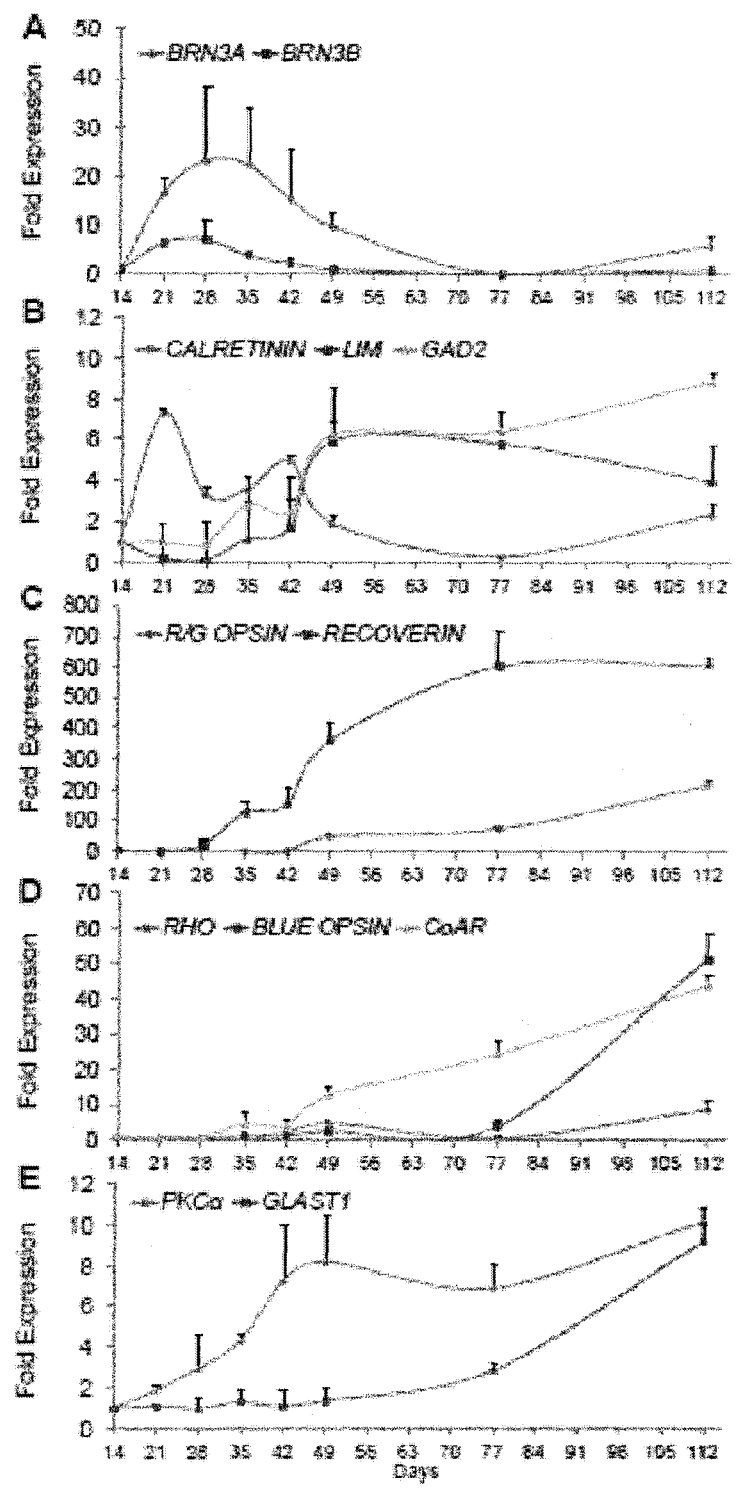
Figure 9 A-E

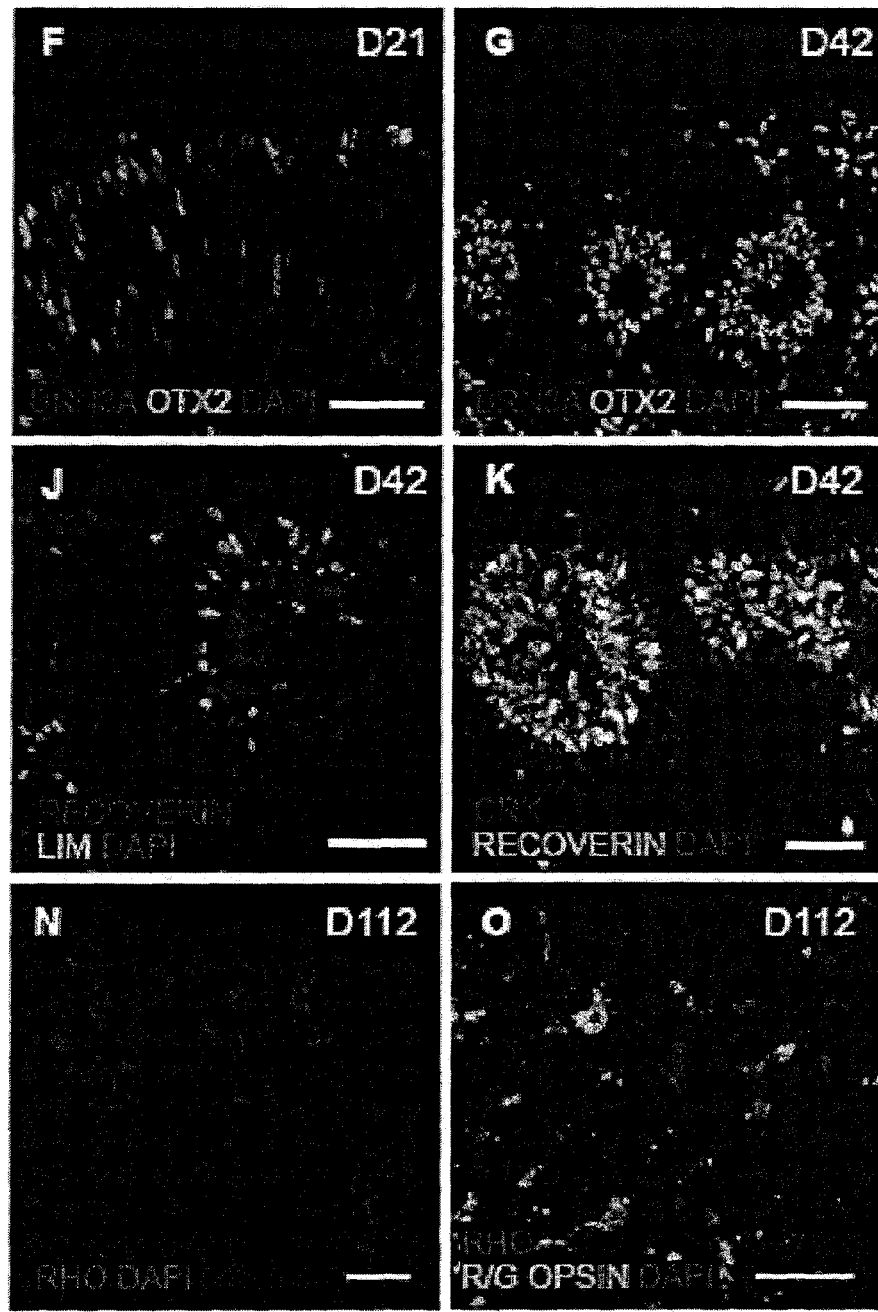
Figure 9 F-O

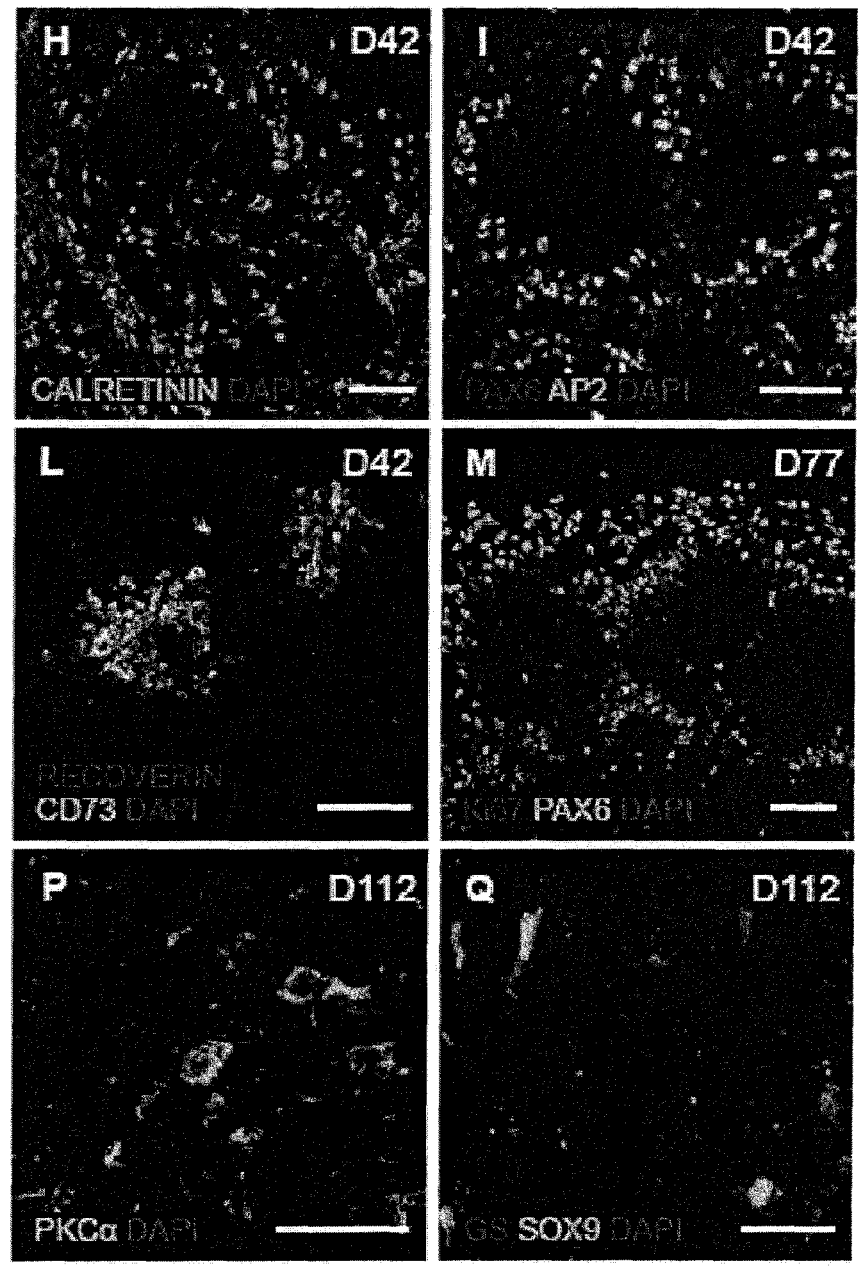
Figure 9 H-Q

METHODS FOR OBTAINING RETINAL PROGENITORS, RETINAL PIGMENTED EPITHELIAL CELLS AND NEURAL RETINAL CELLS

This application is a National Stage Application of PCT/IB2014/061010, filed 25 Apr. 2014, which claims benefit of EP 13165654.8, filed 26 Apr. 2013, which applications are incorporated herein by reference. To the extent appropriate, a claim of priority is made to each of the above disclosed applications.

The impaired or complete loss of function of photoreceptor cells or supporting retinal pigmented epithelium (RPE) is the main cause of irreversible blindness in retinal diseases, such as inherited retinal degenerations and age-related macular degeneration (AMD). Retinal ganglion cell (RGC) death in glaucoma also results in irreversible loss of vision. Rescuing the degenerated retina is a major challenge and cell replacement is one of the most promising approaches (Pearson et al., 2012; Barber et al., 2013). The use of human pluripotent stem cells, embryonic stem (ES) cells and induced pluripotent stem (iPS) cells opens up new avenue for human retinal degenerative diseases. Human ES (hES) and iPS (hiPS) cells that have the ability to be expanded indefinitely in culture while retaining their pluripotent status could be used as an unlimited source of retinal cells (photoreceptors, RPE and RGCs) for tissue transplantation (reviews in: Comyn et al., 2010; Dahlmann-Noor et al., 2010, Boucherie et al., 2011). However, this new technology still faces many difficulties. In particular, current differentiation procedures are not sophisticated enough to guarantee efficiency and safety. Several publications indicated that hES and hiPS cells can be relatively easily differentiated into RPE cells by spontaneous differentiation of colonies in cell cultures (Buchholz et al., 2009; Vaajasaari et al., 2011; Zahabi et al., 2012) or by different floating aggregate methods (Idelson et al., 2009; Lu et al., 2009; Kokkinaki et al., 2011). A growing body of convergent data demonstrated the ability of hES or hiPS to be committed into the neural retinal lineage after embryoid body formation, and further differentiated into cells expressing photoreceptor markers (Lamba et al., 2006, 2009; Osakada et al., 2008, 2009; Meyer et al., 2009, Mellough et al., 2012). The different methods previously developed, though a real advance, still suffer from drawbacks generally associated with the differentiation of pluripotent stem cells into highly specialized cell types. These protocols for photoreceptor-directed differentiation of hES or hiPS cells require several steps, addition of several molecules and are rather inefficient. Recently, other groups went further attempting to obtain 3D structures of optic vesicle-like structures from embryoid bodies of hES or hiPS cells (Meyer et al., 2011; Nakano et al., 2012). Differentiation methods used matrigel in order to recreate a complex extracellular matrix (ECM) around the embryoid bodies, allowing the self formation of a neuroepithelium and a more or less quick differentiation into the photoreceptor cell lineage (Meyer et al., 2011; Nakano et al., 2012; Boucherie et al., 2013; Zhu et al., 2013).

Thus, there is a need in the art for simple, efficient and reliable methods for obtaining substantially pure cultures of certain human neuroepithelial lineage cells, including retinal progenitor cells, RPE cells and neural retinal cells, which accurately model in vitro differentiation and development.

As disclosed in the experimental part below, the inventors have now subjected iPS cells to a new retinal differentiation protocol, combining 2D and 3D culture system. This protocol avoids the formation of embryoid bodies or cell clumps, and can be performed in absence of matrigel or serum. The inventors demonstrated that confluent hiPS cells cultured in pro-neural medium can generate within two weeks neuroepithelial-like structures with an eye field identity, which, when switched to 3D cultures, can differentiate into the major retinal cell types. Under these conditions, hiPS cells self-assembled into neural retina-like tissues, with rapid expression of retinal markers in a developmentally appropriate time window; they gave rise to different retinal cell types such as RGCs and photoreceptors.

A first object of the present invention is hence a method for in vitro obtaining human retinal progenitors, comprising the steps of:
(i) placing an adherent culture of human pluripotent stem cells into a pro-neural medium; and
(ii) maintaining this culture in said pro-neural medium until the appearance of pigmented cells and/or of neuroepithelial-like structures.

In the present text, the "retinal progenitors", also called "retinal progenitor cells", encompass cells which are competent for generating all cell types of the neural retina, including precursors of photoreceptors, as well as cells which can differentiate into RPE.

"Human pluripotent stem cells" include human embryonic stem (hES) cells and human induced pluripotent stem (hiPS) cells. The above method is advantageously performed with human induced pluripotent stem cells.

A "pro-neural medium" herein designates any culture medium which favors the maintenance and/or growth of neuronal cells. Non-limitative examples of such a medium are any medium composed of a nutrient medium, such as Dulbeco's Modified Eagle Medium: Nutrient Mixture F-12 (DMEM/F12) or Neurobasal® Medium (Gibco®), said nutrient medium being supplemented with a medium supplement which comprises at least part of the following elements: carbon sources, vitamins, inorganic salts, amino acids and a protein digest. Non limitative examples of supplements appropriate for obtaining a pro-neural medium are N2, B27, G5 and BIT9500 supplements, as well as any supplement derived from these. The components present in these supplements are summarized in Table 1 below.

TABLE 1

Composition of four medium supplements for pro-neural media.

| | B27[a] | N2[b] | BIT9500[c] | G5[d] |
|---|---|---|---|---|
| BSA | + | − | + | − |
| Transferrin | + | + | + | + |
| Insulin | + | + | + | + |
| Progesterone | + | + | − | − |
| Putrescine | + | + | − | − |
| Sodium selenite | + | + | − | + |
| Biotin | + | − | − | − |
| l-carnitine | + | − | − | − |
| Corticosterone/hydrocortisone | + | − | − | − |
| Ethanolamine | + | − | − | − |
| d(+)-galactose | + | − | − | − |
| Glutathione (reduced) | + | − | − | − |
| Linolenic acid | + | − | − | − |
| Linoleic acid | + | − | − | − |
| Retinyl acetate | + | − | − | − |
| Selenium | + | − | − | − |
| T3 (triodo-1-thyronine) | + | − | − | − |

TABLE 1-continued

Composition of four medium supplements for pro-neural media.

| | B27[a] | N2[b] | BIT9500[c] | G5[d] |
|---|---|---|---|---|
| dl-α-tocopherol (vitamine E) | + | − | − | − |
| dl-α-tocopherol acetate | + | − | − | − |
| Catalase | + | − | − | − |
| Superoxide dismutase | + | − | − | − |
| FGF2 | − | − | − | + |
| EGF | − | − | − | + |

[a]See Brewer et al., 1993;
[b]Provided by manufacturer (Gibco BRL, Germany);
[c]Provided by manufacturer (StemCell Technologies Inc., Canada);
[d]Provided by manufacturer (Life Technologies, USA).

In what precedes, "neuroepithelial-like structures", also named "neural retina-like structures" in the experimental part below, designate phase-bright structures which start to appear after a few days of culture in a pro-neural medium. These structures are essentially made of cells which do not significantly express pluripotency-related genes such as OCT4, and which express transcription factors associated with eye-field specification such as LHX2, RAX, PAX6 and SIX3. As disclosed in the experimental part, when performing the above method, pigmented cells first appear, and the neuroepithelial-like structures most often appear in the vicinity of a patch of pigmented cells.

Of course, when performing the methods according to the present invention, the skilled artisan can detect the expression of various markers (to check either their expression or the fact that they are not expressed anymore, and/or to quantitatively measure their expression level). Any technique known in the art can be used to this aim, such as, for example, quantitative RT-PCR and immunoassays. Examples of markers for pluripotency are OCT4, SOX2 and NANOG; examples of markers for the eye field are RAX, PAX6, OTX2, LHX2 and SIX3, the two first ones being preferred.

Advantageously, the above method can be performed without using complex and costly media. Indeed, very simple media can be used for obtaining human retinal progenitors from an adherent culture of pluripotent stem cells. In particular, differentiation factors are not needed. According to a preferred embodiment of the above method, the pro-neural medium used in the culture step is devoid of at least one of the following differentiation factors: noggin, Dkk-1 and IGF-1. In particular, the pro-neural medium can be devoid of these three factors.

The human pluripotent stem cells used in step (i) can be cultured in any kind of adherent culture system. Non-limitative examples of surfaces which can be used for this culture are: glass, plastic (possibly treated), collagen, laminin, fibronectin, Matrigel™, poly-L-lysin, nutrient cells, or any synthetic surface commercially available such as Corning Synthemax™. In a preferred embodiment, the adherent culture used in step (i) of the above method is in the form of a colony-type monolayer reaching at least 80% confluence. The skilled artisan is familiar with the notion of confluence for adherent cells, and will be able to evaluate this confluence, which can be appreciated locally, i.e., only in one area of the recipient, especially if the confluence is non homogeneous on the whole culture surface. In the case of colony-type monolayers, a "80% confluence" can be defined, if needed, as the situation when some colonies punctually come into contact with other colonies, while some free space (representing between 10 and 30% of the surface) remains between these colonies.

As described in the experimental part, and although this is not compulsory, the method according to the present invention can be performed so that step (i) is preceded by a step of adherent culture of said pluripotent stem cells in a culture medium for maintenance of pluripotent stem cells, modified so that it is devoid of basic fibroblast growth factor (bFGF/FGF2), during 1 to 4 days, preferably during 2 days. Non-limitative examples of appropriate media for this additional step are the Primate ES Cell Medium and the Repro-Stem medium from ReproCELL.

In a particular embodiment of the above method, step (ii) is performed during at least 7 days and preferably between 10 to 14 days, so that a sufficient amount of neuroepithelial-like structures appear. Of course, the method of culture may evolve so that step (ii) can be shortened. As already mentioned above, the neuroepithelial-like structures are essentially made of cells which do not significantly express pluripotency-related genes such as OCT4, and which express transcription factors associated with eye-field specification. Hence, depending on the culture system, the skilled artisan can chose to define the end of step (ii) as the time when at least some cells stop expressing OCT4 and/or start expressing RAX and PAX6. As already mentioned, this characterization can be performed by any known technique, such as qRT-PCR or immunostaining.

According to another aspect, the present invention pertains to a method for obtaining RPE cells, wherein said method comprises the steps of:
(i) placing an adherent culture of human pluripotent stem cells into a pro-neural medium;
(ii) maintaining this culture in said pro-neural medium until the appearance of pigmented cells;
(iii$_{RPE}$) collecting, from the culture obtained in step (ii), at least one pigmented cell; and
(iv$_{RPE}$) culturing the pigmented cell(s) obtained in step (iii$_{RPE}$).

When performing this method, the skilled artisan can check that the cells collected in step (iii$_{RPE}$) express the microphthalmia-associated transcription factor (MITF) and/or ZO-1. As already mentioned, any technique known in the art (such as qRT-PCR and immunostaining) can be used to this aim.

According to a preferred embodiment of the above method for obtaining RPE cells, the culture in step (iv$_{RPE}$) is carried out in an adherent culture system. Any adherent culture system can be used, as already mentioned above.

When performing the method of the invention for obtaining RPE cells, the cells are amplified in step (iv$_{RPE}$) during at least 5 days. Advantageously, the culture of step (iv$_{RPE}$) can be maintained and amplified during several weeks, to obtain great amounts of RPE cells: for example, when about 10 patches of pigmented cells are collected in step (iii$_{RPE}$) and plated together in a new dish of 3 cm$^2$, a substantially pure (99%) confluent adherent culture of RPE cells is obtained after 3 to 4 weeks, or after 10 to 14 days if FGF2 is added to the culture medium (10 ng/ml every 2 to 3 days).

Another aspect of the present invention is a method for obtaining neural retinal cells, wherein said method comprises the steps of:
(i) placing an adherent culture of human pluripotent stem cells into a pro-neural medium;
(ii) maintaining this culture in said pro-neural medium until the appearance of neuroepithelial-like structures;
(iii$_{NR}$) collecting, from the culture obtained in step (ii), cells from at least one neuroepithelial-like structure; and
(iv$_{NR}$) culturing the cells obtained in step (iii$_{NR}$).

The "neural retinal cells" herein include RGC, bipolar cells, horizontal cells, amacrine cells, photoreceptor cells (rod and cones), Müller glial cells as well as precursors of any of these cell types.

Importantly, the various neural retinal cells do not appear at the same time during step ($iv_{NR}$), during which the cultured cells differentiate. Hence, depending on the duration of step ($iv_{NR}$), different cell types will form. The order of appearance is as follows: ganglion cells appear first, followed by amacrine cells and horizontal cells, and photoreceptors appear later. Depending on the cell-type which is needed, the skilled artisan will hence perform the culturing step ($iv_{NR}$) during 21 to 42 days.

As exemplified in the experimental part below, the method according to this aspect of the invention can be performed by collecting, in step ($iii_{NR}$), at least one neuroepithelial-like structure. This can be done, for example, by mechanically separating this structure from the layer of adherent cells. This structure can then be placed, either alone or together with other neuroepithelial-like structures, in another culture recipient, such as a well of a multiwell plate, a Petri dish, a flask, etc.

When performing this method, the skilled artisan can advantageously check that the cells collected in step ($iii_{NR}$) co-express PAX6 and RAX, characteristic of eye field cells. Alternatively or additionally, the expression of the cell proliferation marker Ki67 by the cells collected in step ($iii_{NR}$) can be measured.

According to a particularly advantageous aspect, the present invention pertains to a method for obtaining photoreceptor precursors, comprising the above steps (i) to ($iv_{NR}$), wherein step ($iv_{NR}$) is performed during at least 21 days, preferably at least 28 days. Of course, depending on the future development of the culture conditions, this step may be further shortened.

At any time during step ($iv_{NR}$), the skilled artisan can check the differentiation into the photoreceptor lineage by measuring the expression of NRL and/or CRX in the cultured cells, for example by qRT-PCR. Alternatively or in addition, photoreceptor precursors can be identified with a RECOVERIN immunostaining, as disclosed in the experimental part below. The inventors have also demonstrated that CD73, which can be used as a cell surface marker for cell sorting of photoreceptor precursors, is co-expressed with RECOVERIN. This can advantageously be used by adding a further step of cell sorting of photoreceptor precursors following step ($iv_{NR}$), for example by using an anti-CD73 antibody. The resulting cell population, enriched in photoreceptor precursors, can be used, for example, for cell transplantation or screening approaches.

Optionally, a Notch inhibitor such as DAPT can be added to the culture medium during at least 1 day, preferably during 5 days or more in step ($iv_{NR}$). DAPT is a γ-secretase inhibitor and indirectly an inhibitor of Notch, and the inventors have shown that its addition during a few days in step ($iv_{NR}$) favors the generation of photoreceptor precursors (see Example 2 below and FIG. 5).

According to a preferred embodiment of the method for obtaining neural retinal cells disclosed above, the culture in step ($iv_{NR}$) is carried out in a non-adherent culture system. For example, neuroepithelial-like structures collected in step ($iii_{NR}$) are cultured as floating structures. According to a specific embodiment, each neuroepithelial-like structure collected in step ($iii_{NR}$) is cultured in an individual recipient/well as a floating structure.

Non limitative examples of non-adherent systems include magnetically rotated spinner flasks or shaken flasks or dishes in which the cells are kept actively suspended in the medium, as well as stationary culture vessels or T-flasks and bottles in which, although the cells are not kept agitated, they are unable to attach firmly to the substrate.

As described in the experimental part, the cells or neuroepithelial-like structures can advantageously be kept actively suspended in the medium by performing step ($iv_{NR}$) under shaking conditions. Any shaker can be used for this purpose, such as, for example, a rotator which agitates the cultures in three dimensions.

According to another preferred embodiment of the method of the invention for obtaining neural retinal cells, the culture medium used in step ($iv_{NR}$) is supplemented with FGF2 during at least 5 days. This culture medium is preferably a pro-neuronal medium as defined above.

One advantage of the present invention is that, from a first adherent culture, two different cultures can be performed in parallel in order to obtain both RPE cells (first culture, preferably adherent) and precursors of the neural retina (second culture, preferably non-adherent). Accordingly, the present invention pertains to a method for obtaining both RPE cells and precursors of the neural retina, comprising steps (i) and (ii) as defined above, followed by steps ($iii_{RPE}$) and ($iv_{RPE}$) defined above, performed in parallel with steps ($iii_{NR}$) and ($iv_{NR}$) also disclosed above.

Most importantly, the present invention provides reliable methods to easily and rapidly obtain large amounts of retinal cells of any of the major types (RPE, RGCs, amacrine cells, horizontal cells, Müller glial cells and photoreceptors), with a high degree of purity. For example, a culture comprising more than 75% of photoreceptor precursors can be obtained in less than one month.

It is envisioned that these methods, and the substantially pure cell cultures obtained through them, are useful in the following areas:

- Transplantation/cell therapy: non-limiting examples include the use of RPE cells and/or of retinal progenitor cells or cells differentiated therefrom, in lost cells replacement therapy to help restore previously lost vision. The methods and cultures could also be used for developing tissues for use in whole tissue replacement therapy.
- Drug screening for identifying agents able to protect or enhance the function of all cells, including RGCs, rods, cones and RPE cells. By "agent" is herein meant any kind of molecule or composition, but also non-chemical agents such as any electromagnetic or corpuscular radiation (UV, visible light, ionizing radiation, etc.).
- Producing human retinal disease models from pluripotent cells, especially from hiPS cells, which can also be used to study pathophysiology and for drug screening or customized therapy using stem cells or derivatives thereof
- As a unique model of human neural development, which would be a useful resource to study a variety of processes, including without limitation retinal development, tissue formation, and synapse formation.

The invention is further illustrated by the following figures and examples.

LEGENDS TO THE FIGURES

FIG. 1: Derivation and characterization of integration-free hiPS cells. (A) Schematic diagram depicting the steps involved in the reprogrammation of AHDF. (B) Emergence of heterogeneous hiPS colonies on fibroblasts. (C) Positive alkaline phosphatase staining of well established hiPS cells.

(D, E) Expression of pluripotency markers by immunohistochemistry in hiPS cells (subclone 2). (F) qRT-PCR analysis of pluripotency and self-renewal markers in hiPS cells, AHDF and hES cells (n=3 experiments). Data are normalized on hES cells. (G) qRT-PCR analysis of several germ layer markers in embryoid bodies derived from hiPS cells after two weeks (n=3 experiments). Data are normalized on undifferentiated hiPS cells (H-J) Immunostaining of embryoid bodies derived from hiPS cells (subclone 2) after two weeks for markers of endoderm (SOX17), mesoderm (SMA) and ectoderm (PAX6, TUJI-1). (K) Karyotype analysis of hiPSsubclone 2. (L) PCR screening using primers targeting oriP for the detection of oriP/EBNA1 vectors in the genomic DNA (gDNA) fraction and in the episomal fraction (Epi extract) of hiPSsubclone 2 after 5 (AHDFc2p5) or 15 passages (AHDFc2p15) and from native AHDF as control. Scale bars=100 µm.

FIG. 2: Efficient generation of retinal progenitors from integration-free hiPS cells. (A) Schematic diagram showing the different stages of the differentiation protocol. (B, C) Morphology of hiPS cells differentiating in pro-neural medium after 7 and 14 days. (D) qRT-PCR analysis of eye-field transcription factors (SIX3, LHX2, RAX, PAX6, MITF and VSX2), NRL, CRX and pluripotency marker POU5F1 in neuroepithelial-like structures at D14 (n=3 experiments). Data are normalized on hiPS cells at D0. (E-O) Immunofluorescence staining of D14 neuroepithelial-like structures for PAX6 and RAX (E-G), Ki67 and LHX2 (H-J), or MITF and VSX2 (K-O). Scale bars=100 µm (B, C, E, H and K); 50 µm (F, G, I, J, L-O). (P) qRT-PCR analysis of NOGGIN and DKK1 in hiPSC-2 at D0, D7 and D14. Data are normalized on hiPSC-2 single colonies.

FIG. 3: Differentiation of multiple retinal cell types from floating Neural Retina (NR)-like structures. (A) Schematic illustration outlining the differentiation protocol to generate retinal cells (↻ =3D agitation). (B-D) Morphology of the floating NR-like structures at different times after isolation. (E, F) qRT-PCR analysis of eye-field and photoreceptor specific transcription factors in NR-like structures at different times (n=3 experiments). Data are normalized on NR-like structures cells at D14. (G-I) Immunostaining of D21 NR-like structures for MITF (G), VSX2 (G, H), PAX6 (H), OTX2 (I) and BRN3A (I). (J-L) Immunostaining of NR-like structures for CRX at D14 (J), D21 (K) and D28 (L). (M-N) Immunostaining of D21 NR-like structures for CALRETININ (M) and LIM1 (N). (O) Immunostaining of D28 NR-like structures for RECOVERIN. Scale bars=100 µm (B-D, G-L), 50 µm (M-O).

FIG. 4: Generation and amplification of RPE cells from integration-free hiPS cells. (A) Schematic illustration of the experiment. (B, C) Phase contrast microscopy of hips cells-derived RPE cell monolayer after 30 days. (D) Immunostaining of hips cells-derived RPE cell monolayer after 30 days for ZO-1 and MITF. Scale bars=100 µm. (E) qRT-PCR analysis of mature RPE markers in hiRPE cells at passage 0 (P0), P1 and P2. Data are normalized to control RNA isolated from human adult RPE cells. (F) Evaluation of RPE cell phagocytic activity; Ratio of FITC/DAPI fluorescence in hiRPE cell cultures at P1 and in control RPE-J cell line after 3 hours incubation with FITC-labeled POS. Binding and uptake of POS were assayed as described in the Materials and Methods (Example 1).

Figure 5:
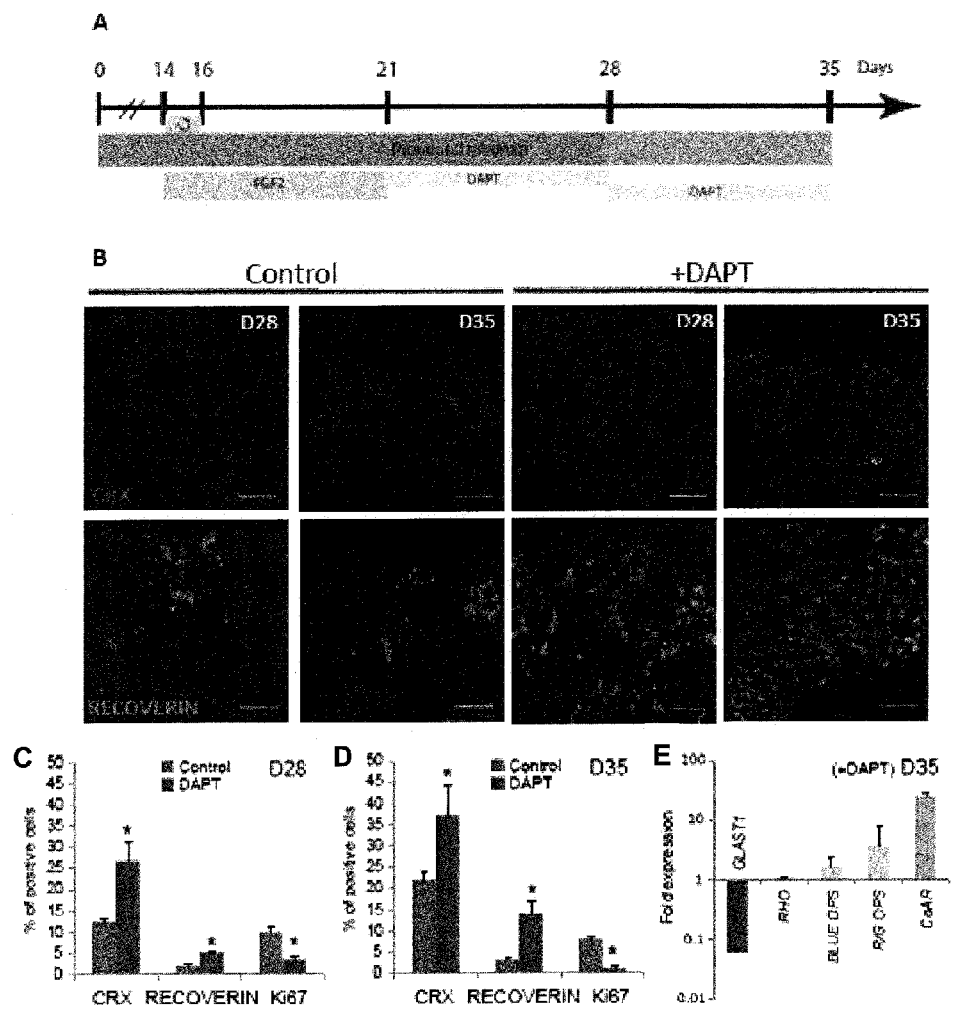

FIG. 5: Acceleration of photoreceptor precursor generation from floating NR-like structures by Notch inhibition. (A) Schematic illustration of the experiment with addition of DAPT either from D21 to D28 or from D28 to D35 (↻ =3D agitation). (B) Immunostaining of NR-like structures at D28 or D35 for CRX and RECOVERIN in the presence or in the absence (control) of DAPT. Scale bars=100 µm. (C and D) Quantification of photoreceptor precursors (CRX, RECOVERIN) and mitotic progenitors (Ki67) at D28 and D35 with or without (control) DAPT. Values represent the mean percentage of positive cells±SEM (n=4, *P<0.05). (E) qRT-PCR analysis of maturing photoreceptor markers and GLAST (marker for Müller glial cells) in D35 NR-like structures treated with DAPT. Data are normalized to NR-like structures at D35 without DAPT treatment. Scale bars=100 µm.

Figure 6:
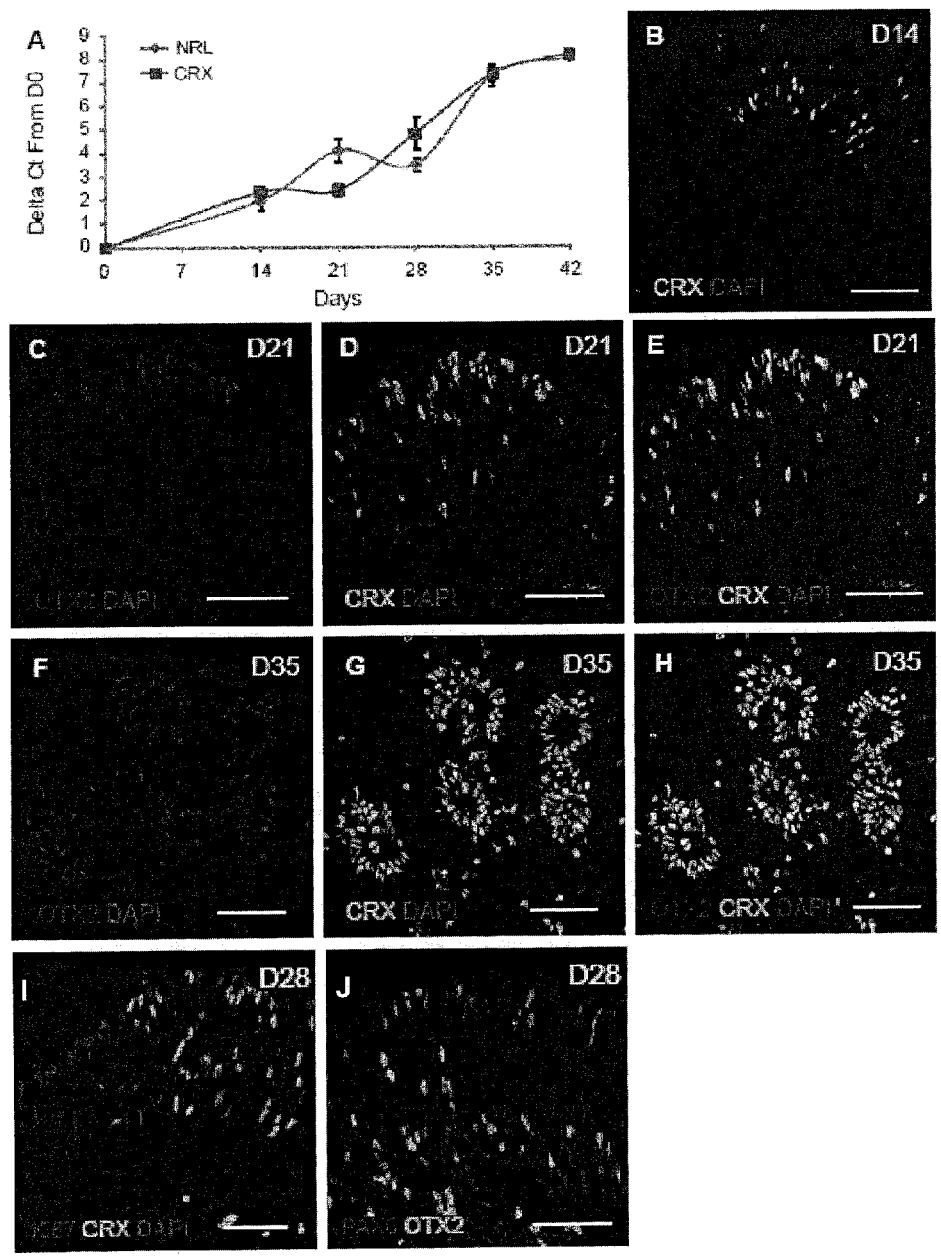

FIG. 6: Early differentiation of photoreceptor precursors in NR-like structures. (A) qRT-PCR analysis of NRL and CRX transcription factors in differentiating NR-like structures. Data are expressed as cycle change in PCR expression level compared to hiPSC-2 at D0. (B) Immunofluorescence staining of cryosectioned NR-like structures at D14 for CRX. (C-H) Immunofluorescence staining of cryosectioned NR-like structures at D21 and D35 for CRX and OTX2. Confocal images demonstrating the colocalization of OTX2 and CRX in sections of NR-like structures at D21 (C-E) and D35 (F-H). (M-N) Immunohistochemistry analysis of cryosectioned NR-like structures at D28 for Ki67 (M) PAX6 (N), OTX2 (N), CRX (M). Scale bars=100 nm (B); 50 nm (C-H and M-N).

Figure 7:
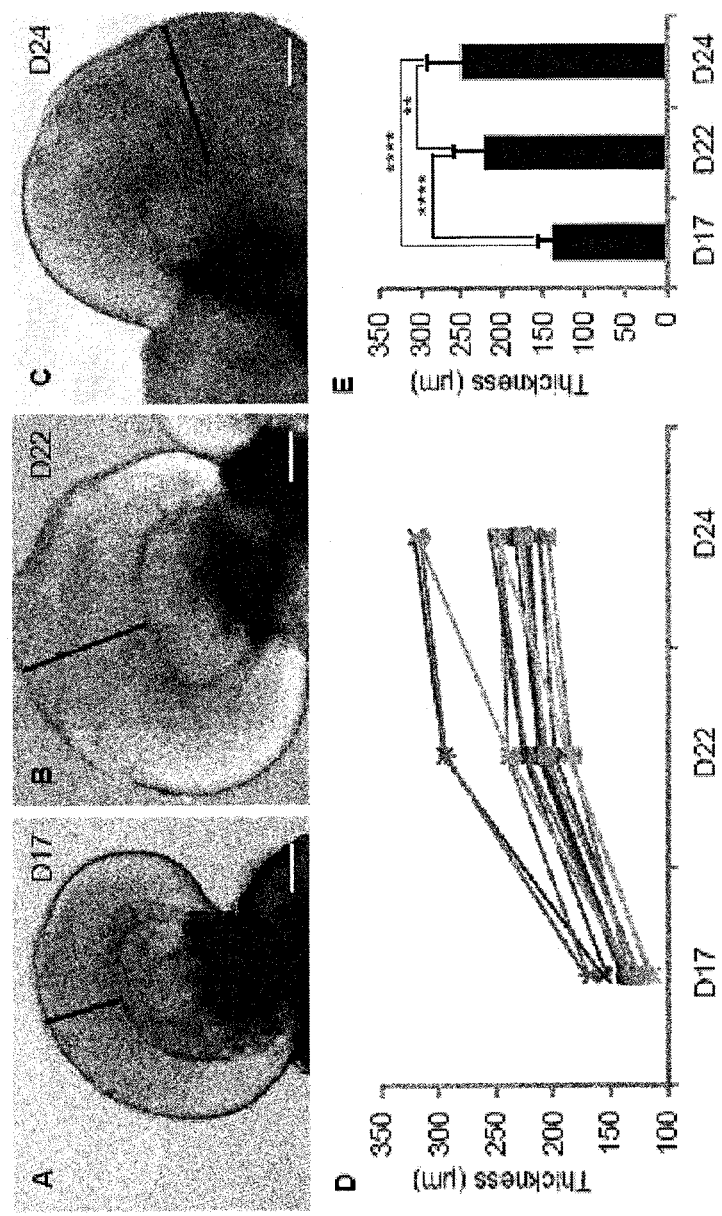

FIG. 7: Thickness analysis of hiPSC-2-derived NR-like structures. (A-C) Thickness evolution (black line) of one representative NR-like structure from D17 to D24. (D) Graphic representation of the thickness evolution of thirteen independent NR-like structures. Each line corresponds to one NR-like structure. (E) Histogram representing the thickness (mean±SEM; P<0.01; **P<0.0001) of the thirteen separate NR-like structures indicating a 80.6±10.2% increase between D17 and D24. Scale bars=100 µm.

Figure 8:
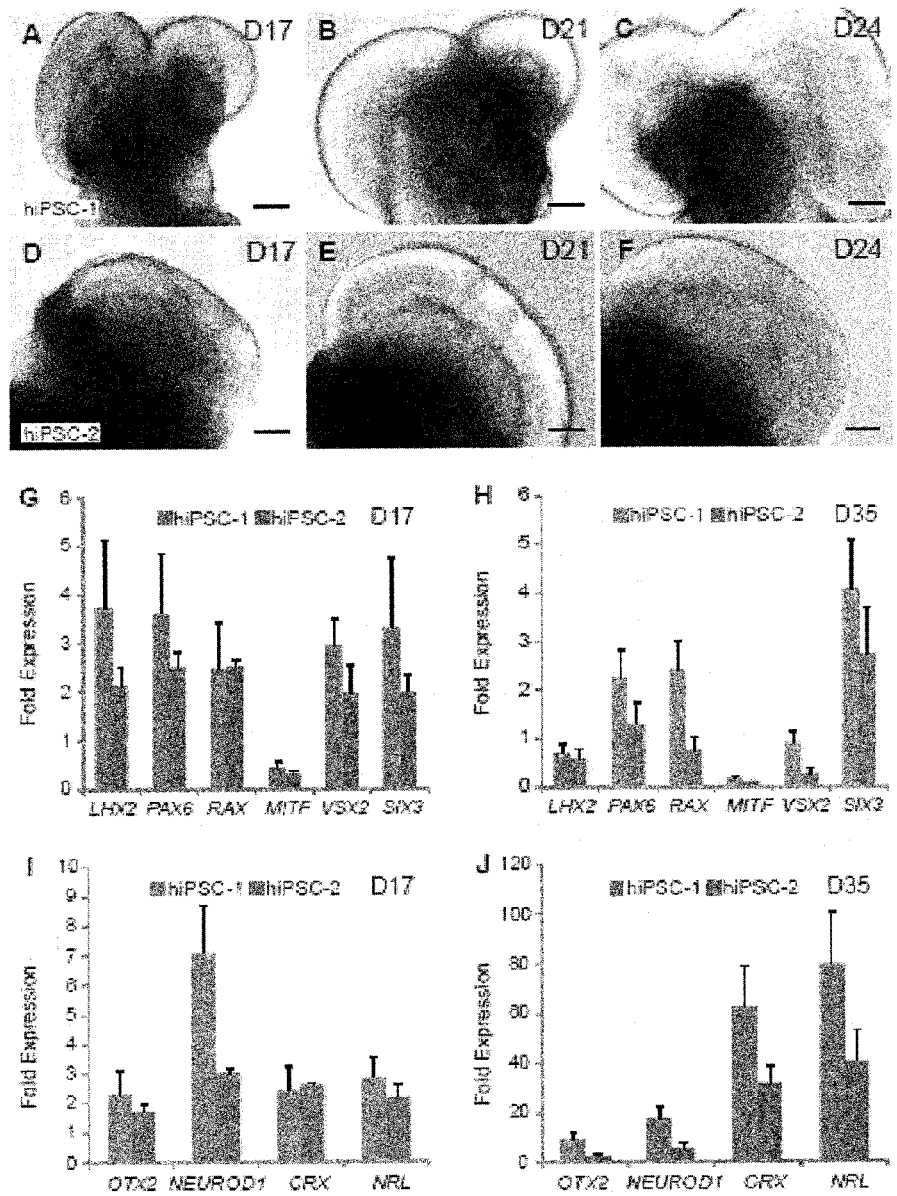

FIG. 8: Reproducibility of the retinal differentiation protocol with different hiPSC clones. (A-C) Morphology of the floating NR-like structures derived from hiPSC-1 at D17, D21 and D24. (D-F) Morphology of the floating NR-like structures derived from hiPSC-2 at D17, D21 and D24. (G and H) qRT-PCR analysis of eye-field transcription factors at D17 and D35 in NR-like structures derived from hiPSC-1 or hiPSC-2. (I and J) qRT-PCR analysis of photoreceptor specific transcription factors at D17 and D35 in NR-like structures derived from hiPSC-1 or hiPSC-2. Data are relative to D14 for each gene. Scale bars=100 µm.

FIG. 9: Differentiation of all retinal cell types from floating NR-like structures. (A-E) qRT-PCR analysis of selected neural retinal cell types in NR-like structures at different times. Data are normalized to NR-like structures at D14 and at D35 for both R/G and BLUE OPSIN. (F-Q) Immunohistochemical analysis of cryosectioned NR-like structure at different stages of differentiation using markers for RGCs (BRN3A, PAX6, CALRETININ), amacrine cells (PAX6, AP2, CALRETININ), horizontal cells (LIM, PAX6, CALRETININ), photoreceptors (OTX2, RECOVERIN, CRX, CD73, CONE ARRESTIN, RHODOPSIN, BLUE and R/G OPSIN), bipolar cells (PKCα), Müller glial cells (GS, SOX9) and for mitotic progenitors (Ki67). Scale bars=50 µm (F-N), 25 µm (O-Q).

Figure 10:
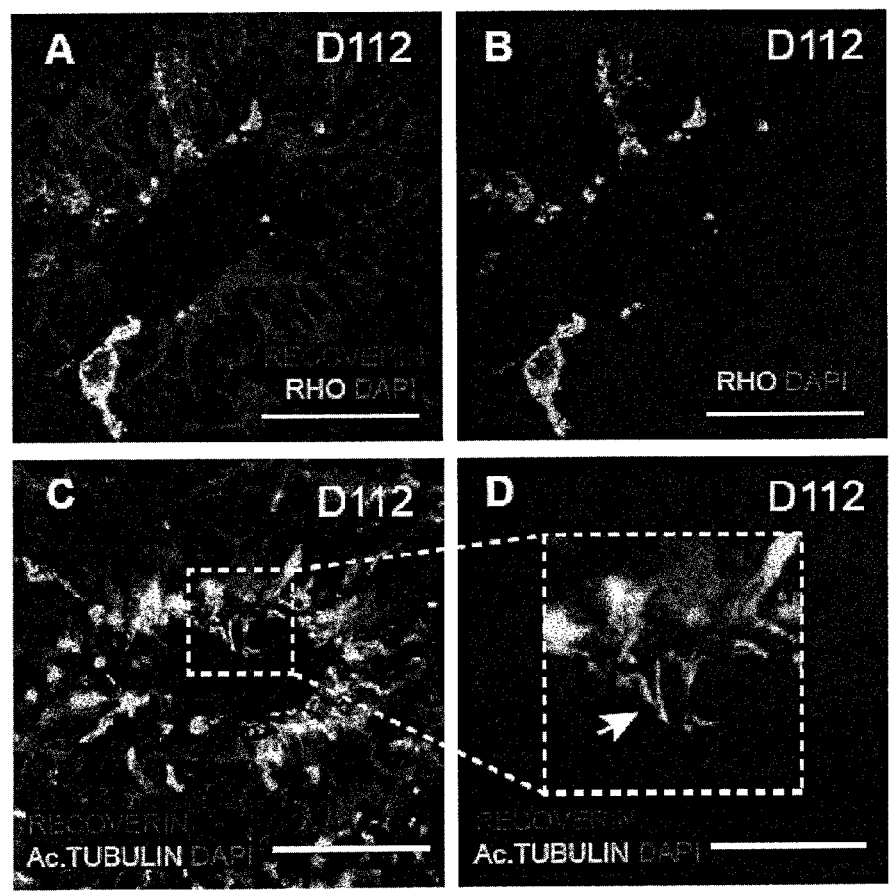

FIG. 10: Presence of mature photoreceptors in NR-like structures after long-term cultures. Immunofluorescence staining of cryosectioned NR-like structures at D112 for RECOVERIN (A-D), RHODOPSIN (A-B) and Acetyl TUBULIN (C-D). Immunohistochemical analysis confirmed the predominant presence of photoreceptors in internal rosettes, with the appearance of acetylated tubulin-positive structures in the luminal zone of the rosettes (arrow in D). Scale bars=25 µm (A-C) and 10 µm (D).

EXAMPLES

Example 1: Reliable and Efficient Differentiation of Human Integration-Free Induced Pluripotent Stem Cells into Retinal Neurons and Retinal Pigmented Epithelial Cells 1.1 Experimental Procedures Human Fibroblast and iPS Cell Cultures Adult Human Dermal Fibroblast (AHDF) from a 8 year old boy (gift from Dr. Rustin, INSERM U676, Paris, France) were cultured in Dulbecco's Modified Eagle Medium (DMEM) high glucose, Glutamax II (Life Technologies) supplemented with 10% FBS (Life Technologies), 1 mM Sodium Pyruvate (Life Technologies), 1×MEM non-essential amino acids (Life Technologies) at 37° C. in a standard 5% $CO_2$/95% air incubator. This medium was called "fibroblast medium". Established human iPS cells were maintained on to mitomycin-C inactivated mouse embryonic fibroblast (MEF) feeder layer (Zenith) in ReproStem medium (ReproCell) with 10 ng/ml of human recombinant fibroblast growth factor 2 (FGF2) (Preprotech). Cells were routinely incubated at 37° C. in a standard 5% $CO_2$/95% air incubator. This medium was called "iPS medium". Cells were manually passaged once a week under the stereomicroscope (Vision Engineering Ltd).

Reprogramming of Human Fibroblasts

The reprogrammation was done with an episomal approach as described (Yu et al., 2009). Briefly, oriP/EBNA1-based episomal vectors pEP4EO2SEN2K (plasmid 20925, Addgene), pEP4EO2SET2K (plasmid 20927, Addgene) and pCEP4-M2L (plasmid 20926, Addgene) were co-transfected into AHDF via nucleofection (Nucleofector 4D, V4XP, with DT-130 program, Lonza). Transfected fibroblasts ($10^6$ cells per nucleofection) were plated directly to 3×10-cm MEF-seeded dishes ($5.10^6$ cells/cm$^2$) in "fibroblast medium". On day 4 post-transfection "fibroblast medium" was replaced with "iPS medium" supplemented with molecules described as increasing the reprogrammation efficiency (Zhang et al. 2013): 500 µM of Valproic acid (Sigma, France), 0.5 µM of PD-0325901 (Selleck, Euromedex, France) and 2 µM of SB431542 (Selleck). After 14 days, cells were cultured in "iPS medium" alone. Between 30 to 40 days, compact cell cluster was cut and transferred into 60 mm Organ Style cell culture dish (Dutscher, France). The emergent hiPS colonies were picked under a stereomicroscope according to their human ES cell-like colony morphology. They were expanded on-to mitomycin-C inactivated MEF feeder layer as described above for subsequent characterization. Complete loss of episomal vectors and non-integration of reprogrammative genes were achieved by PCR as described below.

PCR Analysis of Episomal Vectors

Purification of episomal DNA from hiPS cells was carried out with Nucleospin Plasmid Quick Pure kit (Macherey-Nagel, France) according to manufacturer's protocol. Genomic DNA was isolated using phenol/chloroform extraction method. Due to the nature of purification methods, the genomic purified DNA was likely contaminated with residual amount of episomal DNA from the same cells, and likewise, the purified episomal DNA was contaminated with small amount of genomic DNA, as clearly reported by Yu et al. (2009). PCR reactions were carried out with Go Taq flexi polymerase (Promega, France). For each PCR reaction, 10 µl of genomic or episomal DNA extracted from $10^4$ cells equivalent of containing 100 ng was added as template. The PCR mix contained 1×Go Taq Flexi buffer, 2 mM $MgCl_2$, 0.2 mMdNTPs, 0.5 µM of each primers and 1.25 U of polymerase with the following program: initial denaturation for 1 min at 94° C.; 35 cycles of 94° C. for 45 sec, 60° C. for 30 sec, 72° C. for 1 µM and followed by 72° C. for 5 min. Episomal and genomic DNA from native fibroblasts were used as negative controls and oriP/EBNA1-based episomal vectors (see above, Yu et al. 2009) as positive controls.

Karyotype Analysis

Actively growing hiPS cell colonies (80% confluency) were treated with colchicine (20 mg/ml, Eurobio, France) for 90 min at 37° C. Cells were dissociated with 0.05% Trypsin-EDTA then incubated in 75 mM KCl (Sigma Aldrich) for 10-14 min at 37° C., followed by fixation with 3:1 methyl alcohol/glacial acetic acid. For mFISH karyotyping, fixed cells were hybridized overnight at 37° C. with a denatured "cocktail painting mFISH" probe (MetaSystems, Altussheim, Germany). Slides were washed in successive baths of 1×SSC and 0.4×SSC, and nuclei were stained with 250 ng/ml of diamidino-phenyl-indole (DAPI). Biotinylated probes were revealed using Cy5 MetaSystems B-tect detection kit (MetaSystems). Ten to twenty metaphases were captured using a Zeiss Z1 fluorescence microscope equipped with a UV HBO 100-W lamp coupled to an AxioCam camera (Carl Zeiss, France). All the analyzed metaphases were karyotyped using the MetaSystems Isis software (MetaSystems).

Alcaline Phosphatase (AP) Staining

Human iPS cells in culture on MEFs were fixed with 95% ethanol for 10 min at room temperature. The cells were then rinsed with PBS and incubated for 5 to 10 min at room temperature with a mixture of 5-Bromo-4-chloro-3-indolyl-phosphate (BCIP) and Nitro blue tetrazolium (NBT) (Roche, France) in Tris Buffer pH 9.5 with 5 mM $MgCl_2$ and 0.05% Tween-20. Following staining, the cells were rinsed with PBS before visualization under bright field microscope.

Embryoid Body Formation and Analysis.

Human iPS cells colonies were mechanically detached from the MEF layer under a stereomicroscope (Vision Engineering Ltd.) then cultured in suspension into ultra low attachment culture dishes (Nunc, Dutscher, France) in ReproStem medium. Medium was changed every two other day and EB were cultured for 2 weeks before RNA extraction or immunohistochemistry analysis.

Retinal Differentiation

Human iPS cells were expanded to confluence onto mitomycin-C inactivated mouse MEF feeder layer in iPS medium. At this point, defining as day 0, confluent hiPS cells were cultured in iPS medium without FGF2. After 2 days, the medium was switched to a "proneural medium" composed by Dulbecco's Modified Eagle Medium:Nutrient Mixture F-12 (DMEM/F12, 1:1, L-Glutamine), 1% MEM non-essential amino acids and 1% N2 supplement (Life technologies). The medium was changed every 2-3 days. On day 14, identified neuroepithelial-like structures surrounded by pigmented cells were isolated and individually cultured as floating structures (3D) with "proneural medium" supplemented with 10 ng/ml of FGF2 in 24 well-plates mounted on a 3D Nutator shaker (VWR, France) during the 2 first days and medium was changed every 2-3 days. Isolated structures, when cultured on a shaker platform, remained suspended in the media and usually failed to attach to the bottom of the culture plate. On day 19, 20 or 21, FGF2 was removed and half of the "proneural medium" was changed every 2-3 days for the next several weeks.

For RPE cell cultures, identified pigmented patches were cut between day 7 and 14 without the non pigmented budding structures and transferred onto 0.1% gelatin-coated plates (noted as P0). RPE cells were expanded in "proneural" medium (see above) and the medium was changed every 2-3 days until confluency and cells were dissociated in 0.05% Trypsin-EDTA and seeded on new gelatin-coated plates (considered as passage P1).

RNA Extraction and Taqman Assay

Total RNAs were extracted using Nucleospin RNA II kit (Macherey-nagel, France) according to the manufacturer's protocol, and RNA yields and quality were checked with a NanoDrop spectrophotometer (Thermo Scientific, France). cDNA were synthesized from 500 ng of total RNA using QuantiTect reverse transcription kit (Qiagen) following manufacturer's recommendations. cDNAs synthesized were then diluted at 1/20 in DNase free water before performing quantitative PCR. qPCR analysis was performed on Applied Biosystems real-time PCR systems (7500 Fast System) with custom TaqMan® Array 96-Well Fast plates and TaqMan® Gene expression Master Mix (Applied Biosystems) following manufacturer's instructions. All primers and MGB probes labelled with FAM for amplification were purchased from Applied Biosystems (Life Technologies, France). Results were normalized against 18S and quantification of gene expression was based on the Delta Ct Method in three independent experiments. Control RNA from human adult RPE cells corresponds to RPE cells isolated from dissected eye cups at the fovea level.

Cryosection, Immunostaining and Image Acquisition

For cryosection, retinal-like structures were fixed for 15 min in 4% paraformaldehyde (PFA) at 4° C. and washed in PBS. Structures were incubated at 4° C. in PBS/30% Sucrose (Sigma) solution during minimum 2 hours. Structures were embedded in PBS, 7.5% Gelatin (Sigma), 10% Sucrose solution and frozen in isopentane at −50° C. and 10 µm-thick cryosections were collected.

Immunofluorescence staining of sections was performed as previously described (Roger et al. 2006). Briefly, slides were incubated for 1 hr at room temperature with blocking solution (PBS, 0.2% gelatin and 0.25% Triton X-100) and then with the primary antibody (see Table 2) overnight at 4° C. Slides were washed three times in PBS with Tween 0.1% (PBT) and then incubated for 1 hour with appropriate secondary antibody conjugated with AlexaFluor 488 or 594 (Life Technologies) diluted at 1:600 in blocking buffer with 1:10000 DAPI. Fluorescent staining signals were captured with a DM6000 microscope (Leica) equipped with a CCD CoolSNAP-HQ camera (Roper Scientific) or using an Olympus FV1000 confocal microscope equipped with 405, 488 and 543 nm lasers. Confocal images were acquired using a 1.55 or 0.46 µm step size and each acquisition were the projection of 2-4 stacks or 4-8 optical sections.

TABLE 2

List of antibodies used for immunohistochemistry analysis

| Antigen | Species | Dilution | Source |
| --- | --- | --- | --- |
| Acetylated TUBULIN | Mouse monoclonal | 1:1000 | Sigma |
| AP2 | Mouse monoclonal | 1:100 | DSHB |
| BRACHYURY | Rabbit polyclonal | 1:100 | TEBU |
| BRN3A | Mouse monoclonal | 1:250 | Millipore |
| CALRETININ | Mouse monoclonal | 1:500 | Abcys |
| CD73 | Mouse monoclonal | 1:100 | BioLegend |
| CONE ARRESTIN | Rabbit polyclonal | 1:2000 | Millipore |
| CRX | Mouse monoclonal | 1:5000 | Abnova |
| GLUTAMIN SYNTHASE | Mouse monoclonal | 1:500 | Millipore |
| KI67 | Mouse monoclonal | 1:200 | BD Pharmagen |
| LIM1 (LHX1) | Mouse monoclonal | 1:20 | DSHB |
| LHX2 | Goat polyclonal | 1:100 | Santa Cruz |
| MITF | Mouse monoclonal | 1:200 | DAKO |
| NANOG | Rabbit monoclonal | 1:200 | Cell Signaling |
| OCT4 | Rabbit monoclonal | 1:100 | Cell Signaling |
| OPSIN G/R | Rabbit polyclonal | 1:5000 | Millipore |
| OTX2 | Rabbit polyclonal | 1:5000 | Millipore |
| PAX6 | Rabbit polyclonal | 1:1000 | Millipore |
| PKCα | Rabbit polyclonal | 1:5000 | Santa Cruz |
| RAX/RX | Rabbit polyclonal | 1:10 000 | Abcam |
| RHODOPSIN | Mouse monoclonal | 1:250 | From Dr R Molday |
| RECOVERIN | Rabbit polyclonal | 1:2000 | Millipore |
| SSEA4 | Mouse monoclonal | 1:200 | Cell Signaling |
| SMA | Mouse monoclonal | 1:100 | DAKO |
| SOX9 | Rabbit polyclonal | 1:1000 | Millipore |
| SOX17 | Goat polyclonal | 1:200 | R&D |
| TRA1-81 | Mouse monoclonal | 1:100 | Cell Signaling |
| TUJ1 | Mouse monoclonal | 1:250 | Covance |
| VSX2 (CHX10) | Goat polyclonal | 1:2000 | Santa Cruz |
| ZO1 | Rabbit polyclonal | 1:250 | Life Technologies |

Teratoma Formation Assay

Teratoma formation assay was performed as previously described (Griscelli et al., 2012) with slight modifications. Briefly, 1×106 to 2×106 cells were injected in the rear leg muscle of 6 week—old NOD Scid gamma (NSG) mice (Charles River). After 9 to 10 weeks, teratomas were dissected and fixed in 4% paraformaldehyde. Samples were then embedded in paraffin and sections were stained with Haematoxylin and Eosin.

Phagocytosis Assay

Photoreceptor outer segments (POS) were purified from porcine eyes and covalently labeled with fluorescent dye by incubation with 0.1 mg/ml FITC (isomer-1) according to established procedures (2). RPE-J (immortalized rat RPE cell line) at passage 3 and hiRPE cells at passage 1 were placed in individual wells of a 96-well tissue culture plate. Each well was layered with 100 µL of DMEM containing 1×106 POS particles and was incubated at 32° C. (RPE-J) or 37° C. (hiRPE) for 3 hours before rinsing filters the wells three times with PBS containing 1 mM MgCl2 and 0.2 mM CaCl2 (PBS-CM). For exclusive detection of internalized particles, fluorescence of surface-bound FITC-POS was selectively quenched by incubation in 0.2% trypan blue in PBS-CM for 10 min before cell fixation. Cells were fixed by incubation in ice cold methanol for 5 min followed by rehydration and incubation in with DAPI for 10 min at room temperature. Fluorescent signals were quantified with the Infinite M1000 Pro (Tecan) plate reader. The RPE-J cell line was used as a positive control for phagocytic activity and hiRPE cells in the absence of POS were used as a negative control.

Statistical Analysis

Analysis of variance was realized either with the non parametric Friedman test followed by the Dunn's multiple comparison test or the Mann-Whitney test for all pair wise analysis (Prism 6, GraphPad software). Values of P<0.05 were considered statistically significant.

1.2 Results

Generation and Characterization of Human Integration-Free iPS Cells

Adult human dermal fibroblasts (AHDF) were co-transfected with three plasmids coding for OCT4, NANOG, SOX2, LIN28, KLF4 and cMYC, corresponding to plasmid vectors previously described by Yu et al. (2009). Transfected fibloblasts were cultured in "iPS medium", in presence of small molecules (FIG. 1A), previously described as accelerating reprogramming process and reducing episomal vector loss (Zhang et al. 2012). ES-like colonies first became visible approximately between day 30 and 40 post-transfection with a tightly packed dome-like structure (FIG. 1B). When picked and expanded, these hiPS cell colonies showed typical human ES cells morphology. Analysis of these hiPS cells demonstrated that the clones developed Alkaline Phosphatase (AP) activity along with expression of the pluripotent markers Nanog, TRA-1-81, OCT4 and SSEA4 (FIG. 1C-E). TaqMan probe based on qRT-PCR revealed that the expression pluripotent genes markedly increased over the respective fibroblast population and were comparable to that seen in human ES cells (FIG. 1I). iPS colonies could be differentiated in vitro into derivatives of all three germ layers, as observed by TaqMan probe based on qRT-PCR (FIG. 1J) and immunohistochemistry on embryoid bodies after two weeks in culture (FIG. 1F-H). Furthermore, human iPS cell line exhibited a normal karyotype (FIG. 1K). hiPS cells showed no genomic integration of the transgene and had completely lost episomal vectors after 15 passages as demonstrated by RT-PCR analysis on OriP site in the episome (FIG. 1L). The pluripotency of human iPSC lines was validated by teratoma formation assay.

Differentiation of hiPS Cells to Neuroepithelial-Like Structures with an Eye Field Identity Since a prerequisite for iPS cell differentiation is the shutdown of the self-renewal machinery, FGF2 was removed from the medium to encourage the spontaneous differentiation of confluent iPS cells. FGF2 withdrawal from the culture medium may also promote neuroectoderm induction as nicely demonstrated by Greber et al. (2011) in human ES cells. To favor this differentiation of hiPS cells into a neuroectoderm lineage, colonies were cultured in a proneural medium that contained DMEM/F12 medium with 1% MEM non-essential amino acids and 1% N2 supplement (FIG. 2A). This led to the appearance of pigmented colonies within 4 days. After 7 days, phase-bright structures started to appear close to more than half of patches of pigmented cells (FIG. 2B). Within two weeks, all these structures were organized into neuroepithelial-like structures partly surrounded with a patch of pigmented cells (FIG. 2C), corresponding to 1 to 2 structures per $cm^2$. The other pigmented colonies did not develop neuroepithelial-like structures and the formation of these structures was rarely observed in non pigmented areas. At day 14, TaqMan probe based on qRT-PCR revealed that all formed neuroepithelial-like structures lost expression of the pluripotency-related gene OCT4 (POU5F1) and acquired expression of transcription factors associated with eye field specification such as LHX2, RAX PAX6, SIX3 (FIG. 2D) Immunostaining of the neurepithelial-like structures demonstrated that all the cells co-expressed PAX6 and RAX (FIG. 2E-G), characteristic of eye field cells (Mathers and Jamrich 2000). Nearly all the cells were LHX2-positives (FIGS. 2H, 2J) and their progenitor state was confirmed using cell proliferation marker Ki67 (FIG. 2H-J). qRT-PCR further demonstrated that expression of MITF and VSX2, two transcription factors involved in retinal specification during optic vesicle/cup formation (Horsford et al. 2005), is increased by 10 and 100 fold respectively at day 14 (FIG. 2D) Immunhistochemistry revealed an opposite gradient of VSX2 and MITF expression, with the most intense staining for VSX2 in the neuroepithelial-like structures, while the strongest MITF expression was found to the peripheral pigmented part of the structures (FIG. 1K-O). Taken together, these findings demonstrate that neuroepithelial-like structures have a marker expression profile typical for neural retinal progenitors and can be renamed Neural Retinal (NR)-like structures. Interestingly, qRT-PCR revealed that expression of transcription factors of photoreceptor precursors such as NRL and CRX is increased by 5 fold in NR-like structures as early as after 14 days in culture (FIG. 2D), suggesting that some retinal progenitors could already be engaged in the photoreceptor lineage.

Gene expression analysis revealed endogenous expression of Wnt and BMP antagonists, DKK1 and NOGGIN, in confluent hiPSC cultures and both genes were up-regulated during the formation of the neuroepithelial-like structures (FIG. 2P).

Retinal Progenitors Derived from hiPS Cells Differentiate Efficiently into Retinal Neurons The whole structures, corresponding to the NR-like structures with the surrounding pigmented patch of cells (FIG. 2C) were mechanically isolated at day 14 and further cultured as floating structures under 3D agitation (FIG. 3A). Floating structures were cultured in presence of FGF2 in order to favor neural retinal differentiation rather than differentiation into the RPE lineage (Fuhrmann 2010; Martinez-Morales et al. 2004). One day after the isolation (day 15), the NR-like structure had formed a hollow sphere, which continued to increase in size during the culture (FIG. 3B-D). Quantitative analysis showed an increase in thickness of the neuroepithelium from 139±19 µm to 251±41 µm between D17 and D24 (FIG. 7). The inventors analyzed the time course and the acquisition of specific retinal phenotypes, using both qRT-PCR by isolating RNA from the growing sphere and immunohistochemistry. Throughout the differentiation process from day 14 to day 42, transcription factors involved in retinal specification and differentiation, such as LHX2, RAX, SIX3, PAX6, VSX2 and MITF were still expressed (FIG. 3E). At day 21, cells expressing VSX2 were located in the developing neuroeptithelium of the NR-like structure, and MITF-positive cells were exclusively found in the RPE cells in the periphery of the structures (FIG. 3G). The restriction of MITF expression in the RPE cells was confirmed by the decrease of its mRNA expression in the NR-like structure (FIG. 1E). VSX2-positive cells were predominantly located along the outer part of the neuroepithelium and also express PAX6 (FIG. 3H). PAX6-positive/VSX2-negative cells congregated in the inner part of the neuroepithelium, which could correspond to the first differentiating retinal neurons and did not carry the proliferation marker Ki67. Indeed, as early as day 21, ganglion cells and amacrine cells were identified by immunohistochemistry in the same inner location with antibodies directed again BRN3A (FIG. 3I) or CALRETININ (FIG. 3M). LIM1-positive cells corresponding to differentiating horizontal cells were also found in the developing neuroepithelium (FIG. 3N). The expression of OTX2 and NEUROD1, two genes coding for transcription factors involved in the differentiation of retinal cells such as photoreceptors (Basset and Wallace 2012), largely increased during the floating culture (FIG. 3E) Immunohistochemical analysis showed the expression of OTX2 in the RPE cells in the periphery of the structures and the appearance of OTX2-positive cells into the neuroepithelium (FIG. 3I), corresponding to the committed precursors of photoreceptors (Nishida et al., 2003). The differentiation into the photoreceptor lineage is confirmed by the large increase of NRL and CRX expression by qRT-PCR from day 14 to day 42 (FIG. 3F and FIG. 6A). CRX-positive cells were identifiable in the neuroepithelium as early as day 14 (FIG. 3J), with a progressive increase in number at day 21 and 28 (FIG. 3K, L). At this stage, photoreceptor precursors were identified with a RECOVERIN immunostaining (FIG. 3O).

At D21, CRX$^+$ cells co-expressed with OTX2 in the neuroepithelium (FIG. 6C-H). At D28, CRX was essentially expressed in post-mitotic Ki67– cells (FIG. 6M). As expected (Nishida et al., 2003), OTX2$^+$ committed photoreceptor precursors did not express PAX6 (FIG. 6N). All these data demonstrate that these culture conditions allow the differentiation of hiPS cells into the major types of retinal cells (ganglion cells, amacrine/horizontal cells and photoreceptors) in 3 weeks. Moreover, the protocol developed here showed a good reproducibility when two distinct non integrative hiPSC lines (hiPSC-1 and hiPSC-2) were compared (FIG. 8).

Generation of RPE Cells from hiPS Cells

Given the fast appearance of pigmented patch of cells from confluent hiPS cells cultured in proneural medium, the inventors sought to isolate and differentiate them to RPE cells. Between day 7 and 14, pigmented patch of cells were mechanically selected and replated onto gelatin-coated plates for expansion (FIG. 4A). After three weeks to one month, they formed a confluent cell monolayer that displayed the classical cobblestone morphology of RPE cells (FIG. 4B-C). Most cells were immunoreactive for a key RPE specific transcription factor, MITF, and cell-to-cell interfaces were lined by ZO-1, a tight junction marker of the retinal pigmented epithelium (FIG. 4D). qRT-PCR analysis, normalized to adult human RPE cells, demonstrated that hiRPE cells retained the expression of mature RPE-associated markers such as MERTK, RPE65, BEST1 and PEDF, after several passages (FIG. 4E). To determine whether hiRPE cells were functional, their ability to carry out phagocytosis of FITC-labeled photoreceptor outer segments (POS) was tested. A pronounced phagocytosis activity was detected, as efficient as for the control RPE-J cell line with an average of 30% internalized POS within 3 hours (FIG. 4F).

Example 2: Differentiation of Retinal Progenitor Cells into Late-Born Retinal Cell Types Prolonged maintenance of isolated NR-like structures in floating culture allowed further differentiation of the RPCs into the late-born retinal cell types as demonstrated by qRT-PCR (FIG. 9A-E). Indeed, after the first expression of early-born retinal markers of maturing RGCs (BRN3A and B), amacrine (CALRETININ and GAD2), and horizontal (LIM) cells (FIGS. 9A and B), the emergence of markers of late-born retinal cell types was observed, corresponding to cone (R/G OPSIN, BLUE OPSIN and CONE ARRESTIN) and rod photoreceptors (RHODOPSIN and RECOVERIN) (FIGS. 9C and D), bipolar (PKCα) and Müller glial cells (GLAST1) (FIG. 9E). Between D21 (FIG. 9F) and D42 (FIG. 9G), most of the NR-like structures lost their laminar appearance and developed internal rosettes that contained OTX2$^+$, CRX$^+$ and RECOVERIN$^+$ cells, corresponding to the differentiating photoreceptors (FIGS. 9G, J-L and FIG. 6F-H), surrounded by cells that expressed different markers of RGCs (BRN3A and CALRETININ), amacrine (CALRETININ and AP2) and horizontal (LIM) cells (FIG. 9G-J). Interestingly, at D42, RECOVERIN$^+$ cells expressed the cell surface marker CD73 (FIG. 9L), a marker used for cell sorting of photoreceptor precursors for transplantation (Eberle et al., 2011). At D77, PAX6 was present only outside the rosettes in post-mitotic cells (KI67$^-$), consistent with its expression in RGCs, amacrine and horizontal cells (FIG. 9M). By D112, RHODOPSIN and R/G OPSIN appeared in NR-like structures, reflecting the maturation of both rods and cones (FIG. 9N, O). RECOVERIN$^+$ and RHODOPSIN$^+$ cells were commonly localized at the most inner part of the residual rosettes at D112 (FIGS. 10A and B). Interestingly, immunohistochemistry using the connecting cilium marker acetylated TUBULIN revealed the existence of very thin structures in the luminal zone of rosettes juxtaposed to RECOVERIN$^+$ cells, suggesting the formation of potential cilia and photoreceptor outer segments (FIGS. 10C and D). The differentiation of the two other late-born retinal cell types, bipolar and Müller glial cells also required a longer time in culture (D112) to be detected respectively by PKCα staining (FIG. 9P) and by co-expression of glutamine synthetase (GS) and SOX9 (FIG. 9Q). Thereby, these cell culture conditions allowed the generation of all retinal cell types from the RPCs present in the NR-like structures in a sequential manner.

Example 3: Acceleration of Photoreceptor Precursor Generation by Notch Inhibition Immunohistochemical analysis with antibodies against CRX and RECOVERIN demonstrated that the number of photoreceptor precursors gradually increased between D14 (FIG. 3J) and D28 (FIG. 3L, FIG. 5B). Between day 21 and day 35, the NR-like structures lost their laminar structures and developed internal rosettes that contain CRX and RECOVRIN-positive cells (FIG. 5B). Interestingly, the addition of Notch inhibitor DAPT at day 21 for 7 days is sufficient to dramatically increase the number of both CRX- and RECOVERIN-positive cells (FIG. 5B). Later treatment with DAPT, from day 28 to day 35, also led to a large increase in the number of cells expressing CRX and RECOVERIN (FIG. 5B). A one-week treatment with DAPT between D21 and D28 enabled enhanced generation of photoreceptor precursors, since at D28 the number of CRX$^+$ and RECOVERIN$^+$ cells increased 2.2- and 2.6-fold, respectively, compared to the control (FIG. 5C). Concomitantly, the population of mitotic progenitors evaluated at D28 by Ki67 staining largely decreased (3-fold) after treatment at D28 (FIG. 5C). The effect of Notch inhibition was also evaluated between D28 and D35, rather than prolonged exposure to DAPT, because few RPCs remained at D28 after DAPT treatment. Under these conditions, Notch inhibition also led to an increase in the number of photoreceptor precursors within the NR-like structures, namely a 1.7- and 4.1-fold increase at D35 in the number of CRX$^+$ and RECOVERIN$^+$ cells, respectively (FIG. 5D). Interestingly, CONE-ARRESTIN$^+$ cells, that were not normally detected at D35, could be clearly identified at that time after DAPT treatment (not shown). Moreover, qRT-PCR analysis confirmed the increase in CONE-ARRESTIN expression at D35 after DAPT treatment, while no significant changes in gene expression of RHODOPSIN, BLUE OPSIN nor G/R OPSIN were observed (FIG. 5E). GLAST1 expression was decreased after DAPT treatment (FIG. 5E).

These findings demonstrate that Notch signaling slows down the photoreceptor differentiation from hiPS cells, as recently suggested for hES cells (Nakano et al. 2012), and hence that its inhibition favors photoreceptor differentiation and accelerates the generation of photoreceptor precursors from multipotent RPCs.

Example 4: Discussion

This study shows the novel finding that simple culture of confluent hiPSCs in a serum free proneural medium is sufficient to generate NR-like structures and RPE cells in 2 weeks. The process described herein avoids the steps of EBs formation and selection, addition of inductive molecules such as DKK1, NOGGIN and WNT and/or Matrigel, as well as EBs coating on adherent substrates. Early generated structures present an OV phenotype revealed by co-expression of PAX6 and RAX, and opposite gradient of VSX2 and MITF between the neuroepithelium and the RPE. This efficiency is likely due in part to the increasing endogenous production by confluent hiPSCs of DKK1 and NOGGIN, two inducers of neural and retinal specification, generally added for retinal differentiation of hESCS or hiPSCs (Meyer et al., 2011; Boucherie et al., 2013). Nevertheless, previous studies reported that IGF-I added to the culture medium or present in the Matrigel can direct hESCs to a retinal progenitor identity (Lamba et al., 2006; Zhu et al., 2013), suggesting that insulin, already present in the N2 supplement, is sufficient to play a similar role in the above conditions.

Floating cultures of isolated hiPSC-derived NR-like structures allowed the differentiation of the RPCs into all the retinal cell types, in a sequential manner consistent with the in vivo vertebrate retinogenesis, demonstrating the multipotency of hiPSC-derived RPCs. Interestingly, the inventors also report that inhibition of the Notch pathway when RPCs are committed to the photoreceptor lineage clearly enhances the proportion of photoreceptor precursors in the NR-like structures, with a two-fold increase in CRX$^+$ cells. A one-week treatment with the Notch inhibitor, DAPT, is indeed sufficient to induce cell cycle exit for a large majority of the RPCs, allowing the generation after 35 days of about 40% of CRX+ photoreceptor precursors, also expressing cone precursor markers. This strategy is advantageous for the efficient generation of cells with therapeutic applications. NR-like structures did not invaginate to form bilayered cups as elegantly reported in an EBs/Matrigel-dependent protocol using hESCs by Nakano et al. (2012). Instead, the hiPSC-derived structures maintained a laminar organization until D21 and subsequently developed rosettes containing photoreceptor-like cells in the central region, surrounded by both cells with a retinal inner nuclear layer-specific identity and RGCs. Generating mature and stratified NR tissue is however not requisite for future cell therapy strategies based on purified photoreceptor precursors or other retinal-derived cells. In this context, the present protocol allows, in 42 days, the generation of promising candidates for transplantation, i.e., CD73$^+$ photoreceptor precursors. Such precursors have previously been purified and successfully transplanted in mouse retina (Eberle et al., 2011). The possibility of combining NOTCH inhibition and CD73 selection enables the isolation of a large number of transplantable cells, holding great promise for the replacement of degenerated photoreceptors in retinal dystrophies. The ability to produce RGCs from the NR-like structures has important implications for the treatment of glaucoma. In addition to the generation of retinal neurons, the present protocol concomitantly allows the generation of RPE cells (hiRPE) that can be easily passaged and amplified while retaining their phenotype, close to their in vivo state. The present protocol hereby holds great potential to rapidly generate banks of hiRPE cells intended for the future treatment of AMD and other RPE-related diseases.

With the goal of maintaining a clinical grade, the inventors generated hiPSCs by episomal reprogramming, since the use of lentiviral vectors bears a risk of genotoxicity. Autologous feeders can be used for the maintenance of hiPSCs; a xeno-free and feeder-free system will be preferred for regenerative therapy. From a pharmacological perspective, hiPSCs offer valuable potential to profile new compounds in the first process of drug discovery. The proliferative capacity of hiPS-derived RPCs and RPE cells should ensure the development of new cellular tools for phenotype- and target-based high throughput screening with the goal of identifying specific active compounds for future treatments of retinal dystrophies.

This new protocol, which eliminates the need for the time-consuming and labor-intensive manual steps usually required to differentiate hiPSCs into specific retinal lineage, provides a readily scalable approach to generate large numbers of both RPE cells and multipotent RPCs. Thus, in a relatively short period of time, the methods described here produce a source of photoreceptor precursors or RGCs holding the promise for a novel approach to regenerative medicine and pharmaceutical testing/drug screening. This strategy using hiPSCs also provides an opportunity to study the molecular and cellular mechanisms underlying human retinal development and should advance the development of in vitro models of human retinal degenerative diseases.

REFERENCES

Barber, A. C., Hippert, C., Duran, Y., West, E. L., Bainbridge, J. W., Warre-Cornish, K., Luhmann, U. F., Lakowski, J., Sowden, J. C., Ali, R. R., and Pearson, R. A. (2013) Repair of the degenerate retina by photoreceptor transplantation. Proc. Natl. Acad. Sci. USA. 110, 354-359.

Basett, E. A., and Wallace, V. A. (2012) Cell fate determination in the vertebrate retina. Trends Neurosci. 9, 565-573.

Boucherie, C., Mukherjee, S., Henckaerts, E., Thrasher, A. J., Sowden, J. C., and Ali, R. R. (2013) Self-organizing neuroepithelium from human pluripotent stem cells facilitates derivation of photoreceptors. Stem Cells. 31, 408-414.

Boucherie, C., Sowden, J. C., and Ali, R. R. (2011) Induced pluripotent stem cell technology for generating photoreceptors. Regen. Med. 4, 469-479.

Buchholz, D. E., Hikita, S. T., Rowland, T. J., Friedrich, A. M., Hinman, C. R., Johnson, L. V., and Clegg, D. O. (2009) Derivation of functional retinal pigmented epithelium from induced pluripotent stem cells. Stem Cells 27, 2427-2434.

Chen, M., Chen, Q., Sun, X., Shen, W., Liu, B., Zhong, X., Leng, Y., Li, C., Zhang, W., Chai, F., Huang, B., Gao, Q., Xiang, A. P., Zhuo, Y., and Ge, J. (2010) Generation of retinal ganglion-like cells from reprogrammed mouse fibroblasts. Invest. Ophthalmol. Vis. Sci. 11, 5970-5978.

Comyn, O., Lee, E., and MacLaren, R. E. (2010) Induced pluripotent stem cell therapies for retinal disease. Curr. Opin. Neurol. 1, 4-9.

Dahlmann-Noor, A., Vijay, S., Jayaram, H., Limb, A., and Khaw, P. T. (2010) Current approaches and future prospects for stem cell rescue and regeneration of the retina and optic nerve. Can. J. Ophthalmol. 4, 333-341.

Eberle D, et al. (2011) Increased integration of transplanted CD73-positive photoreceptor precursors into adult mouse retina. Invest Ophthalmol Vis Sci 52: 6462-71.

Fuhrmann, S. (2010) Eye morphogenesis and patterning of the optic vesicle. Curr. Top. Dev. Biol. 93, 61-84.

Greber, B., Coulon, P., Zhang, M., Moritz, S., Frank, S., Müller-Molina, A. J., Araúzo-Bravo, M. J., Han, D. W., Pape, H. C., and Schöler, H. R. (2011) FGF signalling inhibits neural induction in human embryonic stem cells. EMBO J. 30, 4874-4784.

Griscelli F, et al. (2012) Malignant germ cell-like tumors, expressing Ki-1 antigen (CD30), are revealed during in vivo differentiation of partially reprogrammed human-induced pluripotent stem cells. Am J Pathol 180: 2084-96.

Horsford, D. J., Nguyen, M. T., Sellar, G. C., Kothary, R., Arnheiter, H., and McInnes, R. R. (2005) Chx10 repression of Mitf is required for the maintenance of mammalian neuroretinal identity. Development 1, 177-187.

Idelson, M., Alper, R., Obolensky, A., Ben-Shushan, E., Hemo, I., Yachimovich-Cohen, N., Khaner, H., Smith, Y., Wiser, O., Gropp, M., Cohen, M. A., Even-Ram, S., Berman-Zaken, Y., Matzrafi, L., Rechavi, G., Banin, E., and Reubinoff, B. (2009) Directed differentiation of human embryonic stem cells into functional retinal pigment epithelium cells. Cell Stem Cell 5, 396-408.

Kokkinaki, M., Sahibzada, N., and Golestaneh, N. (2011) Human induced pluripotent stem-derived retinal pigment epithelium (RPE) cells exhibit ion transport, membrane potential, polarized vascular endothelial growth factor secretion, and gene expression pattern similar to native RPE. Stem Cells 5, 825-835.

Jagatha, B., Divya, M. S., Sanalkumar, R., Indulekha, C. L., Vidyanand, S., Divya, T. S., Das, A. V., and James, J. (2009) In vitro differentiation of retinal ganglion-like cells from embryonic stem cell derived neural progenitors. Biochem. Biophys. Res. Commun 380, 230-235.

Jin, Z. B., Okamoto, S., Xiang, P., and Takahashi, M. (2012) Integration-free induced pluripotent stem cells derived from retinitis pigmentosa patient for disease modeling. Stem Cells Transl. Med. 6, 503-509.

Lamba, D. A., Karl, M. O., Ware, C. B., and Reh, T. A. (2006) Efficient generation of retinal progenitor cells from human embryonic stem cells. Proc. Natl. Acad. Sci. USA 103, 12769-12774.

Lamba, D. A., Gust, J. and Reh, T. A. (2009) Transplantation of human embryonic stem cell-derived photoreceptors restores some visual function in Crx-deficient mice. Cell Stem Cell 1, 73-79.

Lu, B., Malcuit, C., Wang, S., Girman, S., Francis, P., Lemieux, L., Lanza, R., and Lund, R. (2009) Long-term safety and function of RPE from human embryonic stem cells in preclinical models of macular degeneration. Stem Cells. 9, 2126-2135.

Martinez-Morales, J. R., Rodrigo, I., and Bovolenta, P. (2004) Eye development: a view from the retina pigmented epithelium. Bioessays. 7, 766-777.

Mathers, P. H., and Jamrich M. (2000) Regulation of eye formation by the Rx and pax6 homeobox genes. Cell. Mol. Life Sci. 2, 186-194.

Mellough, C. B., Sernagor, E., Moreno-Gimeno, I., Steel, D. H., and Lako, M. (2012) Efficient stage-specific differentiation of human pluripotent stem cells toward retinal photoreceptor cells. Stem Cells 30, 673-686.

Meyer, J. S., Shearer, R. L., Capowski, E. E., Wright, L. S., Wallace, K. A., McMillan, E. L., Zhang, S. C., and Gamm, D. M. (2009) Modeling early retinal development with human embryonic and induced pluripotent stem cells. Proc. Natl. Acad. Sci. USA 106, 16698-16703.

Meyer, J. S., Howden, S. E., Wallace, K. A., Verhoeven, A. D., Wright, L. S., Capowski, E. E., Pinilla, I., Martin, J. M., Tian, S., Stewart, R., Pattnaik, B., Thomson, J. A., and Gamm, D. M. (2011) Optic vesicle-like structures derived from human pluripotent stem cells facilitate a customized approach to retinal disease treatment. Stem Cells 29, 1206-1218.

Nakano, T., Ando, S., Takata, N., Kawada, M., Muguruma, K., Sekiguchi, K., Saito, K., Yonemura, S., Eiraku, M., and Sasai, Y. (2012) Self-formation of optic cups and storable stratified neural retina from human ESCs. Cell Stem Cell 10, 771-785.

Nishida, A., Furukawa, A., Koike, C., Tano, Y., Aizawa, S., Matsuo, I., and Furukawa, T. (2003) Otx2 homeobox gene controls retinal photoreceptor cell fate and pineal gland development. Nat. Neurosci. 12, 1255-1263.

Osakada, F., Ikeda, H., Mandai, M., Wataya, T., Watanabe, K., Yoshimura, N., Akaike, A., Sasai, Y., and Takahashi, M. (2008) Toward the generation of rod and cone photoreceptors from mouse, monkey and human embryonic stem cells. Nat. Biotechnol. 26, 215-224.

Osakada, F., Jin, Z. B., Hirami, Y., Ikeda, H., Danjyo, T., Watanabe, K., Sasai, Y., and Takahashi, M. (2009) In vitro differentiation of retinal cells from human pluripotent stem cells by small-molecule induction. J. Cell. Sci. 122, 3169-3179.

Parameswaran, S., Balasubramanian, S., Babai, N., Qiu, F., Eudy, J. D., Thoreson, W. B., and Ahmad, I. (2010) Induced pluripotent stem cells generate both retinal ganglion cells and photoreceptors: therapeutic implications in degenerative changes in glaucoma and age-related macular degeneration. Stem Cells 4, 695-703.

Pearson, R. A., Barber, A. C., Rizzi, M., Hippert, C., Xue, T., West, E. L., Duran, Y., Smith, A. J., Chuang, J. Z., Azam, S. A., Luhmann, U. F., Benucci, A., Sung, C. H., Bainbridge, J. W., Carandini, M., Yau, K. W., Sowden, J. C., and Ali, R. R. (2012) Restoration of vision after transplantation of photoreceptors. Nature 485, 99-103.

Roger, J., Brajeul, V., Thomasseau, S., Hienola, A., Sahel, J-A., Guillonneau, X., and Goureau, O. (2006) Involvement of Pleiotrophin in CNTF-mediated differentiation of the late retinal progenitor cells. Dev. Biol. 298, 527-539.

Tucker, B. A., Anfinson, K. R., Mullins, R. F., Stone, E. M., and Young, M. J. (2013) Use of a synthetic xeno-free culture substrate for induced pluripotent stem cell induction and retinal differentiation. Stem Cells Transl. Med. 1, 16-24.

Zahabi, A., Shahbazi, E., Ahmadieh, H., Hassani, S. N., Totonchi, M., Taei, A., Masoudi, N., Ebrahimi, M., Aghdami, N., Seifinejad, A., Mehrnejad, F., Daftarian, N., Salekdeh, G. H., and Baharvand, H. (2012) A new efficient protocol for directed differentiation of retinal pigmented epithelial cells from normal and retinal disease induced pluripotent stem cells. Stem Cells Dev. 21, 2262-2272.

Vaajasaari, H., Ilmarinen, T., Juuti-Uusitalo, K., Rajala, K., Onnela, N., Narkilahti, S., Suuronen, R., Hyttinen, J., Uusitalo, H., and Skottman, H. (2011) Toward the defined and xeno-free differentiation of functional human pluripotent stem cell-derived retinal pigment epithelial cells. Mol. Vis. 17, 558-575

Yu, J., Hu, K., Smuga-Otto, K., Tian, S., Stewart, R., Slukvin, I. I., and Thomson, J. A. (2009) Human induced pluripotent stem cells free of vector and transgene sequences. Science 324, 797-801.

Zhang, Y., Li, W., Laurent, T., and Ding, S. (2012) Small molecules, big roles—the chemical manipulation of stem cell fate and somatic cell reprogramming. J. Cell. Sci. 125, 5609-5620.

Zhu, Y., Carido, M., Meinhardt, A., Kurth, T., Karl, M. O., Ader, M., and Tanaka, E. M. (2013) Three-dimensional neuroepithelial culture from human embryonic stem cells and its use for quantitative conversion to retinal pigment epithelium. PLoS One. 2013; 8(1):e54552.

The invention claimed is:

1. A method for in vitro obtaining human retinal progenitors, comprising the steps of:
    (i) placing an adherent culture of human pluripotent stem cells in a neural cell culture medium, said neural cell culture medium being composed of a nutrient medium supplemented with a medium supplement which comprises at least insulin and wherein the pluripotent stem cells form a colony-type monolayer; and
    (ii) maintaining this culture in said neural cell culture medium until the appearance of pigmented cells and/or of neuroepithelial-like structures.

2. The method of claim 1, wherein said neural cell culture medium is devoid of at least one of the following differentiation factors: noggin, Dkk-1 and IGF-1.

3. The method of claim 2, wherein said neural cell culture medium is devoid of noggin, Dkk-1 and IGF-1.

4. The method of claim 1, wherein, in step (i), the colony-type monolayer reaching at least 80% confluence.

5. The method of claim 1, wherein step (ii) is performed during at least 7 days.

6. The method of claim 1, for obtaining retinal pigmented epithelial cells (RPE cells), wherein said method further comprises the steps of
    ($iii_{RPE}$) collecting, from the culture obtained in step (ii), at least one pigmented cell; and
    ($iv_{RPE}$) culturing the pigmented cell(s) obtained in step ($iii_{RPE}$).

7. The method of claim 6, wherein the culture in step ($iv_{RPE}$) is carried out in an adherent culture system.

8. The method of claim 1, for obtaining neural retinal cells, wherein said method further comprises the steps of:
    ($iii_{NR}$) collecting, from the culture obtained in step (ii), cells from at least one neuroepithelial-like structure; and
    ($iv_{NR}$) culturing the cells obtained in step ($iii_{NR}$).

9. The method of claim 8, wherein at least one neuroepithelial-like structure is collected in step ($iii_{NR}$).

10. The method of claim 8, wherein the culture in step ($iv_{NR}$) is carried out in a non-adherent culture system.

11. The method of claim 8, wherein in step ($iv_{NR}$), the culture medium is supplemented with FGF2 during at least 5 days.

12. The method of claim 8, wherein the culture in step ($iv_{NR}$) is performed under shaking conditions.

13. The method of claim 8, for obtaining photoreceptor precursors, wherein step ($iv_{NR}$) is performed during at least 21 days.

14. The method of claim 13, wherein in step ($iv_{NR}$), a Notch inhibitor is added to the culture medium during at least 1 to 5 days.

15. The method of claim 13, further comprising a step of cell sorting of photoreceptor precursors through binding of the cell surface marker CD73.

16. The method according to claim 7, for obtaining both RPE cells and precursors of the neural retina, wherein steps ($iii_{RPE}$) and ($iv_{RPE}$) are performed in parallel with the steps of steps of:
    ($iii_{NR}$) collecting, from the culture obtained in step (ii), cells from at least one neuroepithelial-like structure; and
    ($iv_{NR}$) culturing the cells obtained in step ($iii_{NR}$).

17. The method of claim 1, wherein the neural cell culture medium is composed of a nutrient medium supplemented with a medium supplement which comprises components selected from a group comprising insulin, transferrin, progesterone, putrescine sodium selenite and combination thereof.

18. The method of claim 1, wherein the neural cell culture medium is composed of a nutrient medium supplemented with a medium supplement which comprises insulin, transferrin, progesterone, putrescine and sodium selenite.

* * * * *